United States Patent [19]

Litman et al.

[11] 4,275,149

[45] Jun. 23, 1981

[54] MACROMOLECULAR ENVIRONMENT CONTROL IN SPECIFIC RECEPTOR ASSAYS

[75] Inventors: David J. Litman, Palo Alto; Zvi Harel, Stanford; Edwin F. Ullman, Atherton, all of Calif.

[73] Assignee: Syva Company, Palo Alto, Calif.

[21] Appl. No.: 964,099

[22] Filed: Nov. 24, 1978

[51] Int. Cl.³ .................. B12Q 1/66; C12N 11/02; C12N 11/10
[52] U.S. Cl. .................................... 435/7; 23/230 B; 424/12; 435/177; 435/178; 435/810; 435/6
[58] Field of Search .................. 23/230 B; 424/1, 15, 424/8, 12; 435/5, 7, 810, 177, 178

[56] References Cited

U.S. PATENT DOCUMENTS

| | | | |
|---|---|---|---|
| 3,791,932 | 2/1974 | Schuurs et al. | 435/7 |
| 4,052,010 | 10/1977 | Baker et al. | 424/12 |
| 4,059,685 | 11/1977 | Johnson | 435/7 |
| 4,067,959 | 1/1978 | Bolz | 435/7 |
| 4,134,792 | 1/1979 | Boguslaski et al. | 435/7 |
| 4,193,983 | 3/1980 | Ullman et al. | 23/230 B X |

OTHER PUBLICATIONS

Wingard, et al., *Applied Biochemistry and Bioengineering*, vol. 1, Academic Press, NY, (1976), pp. 135–138.

*Primary Examiner*—Thomas G. Wiseman
*Attorney, Agent, or Firm*—Bertram I. Rowland

[57] ABSTRACT

Method and compositions are provided for performing protein binding assays involving a homologous pair consisting of ligand and receptor for the ligand. The method employs a label conjugated to a member of said homologous pair and a uniformly dispersed discontinuous phase of discrete particles in a continuous aqueous phase, where the discrete particles create microenvironments which allow for discrimination between the label associated with the particle—in a discontinuous phase——and the label in the continuous phase.

Various conjugates and particles are provided which find use in the subject method.

46 Claims, No Drawings

MACROMOLECULAR ENVIRONMENT CONTROL IN SPECIFIC RECEPTOR ASSAYS

BACKGROUND OF THE INVENTION

1. Field of the Invention

The measurement of trace amounts of a wide variety of organic compounds has become essential in medicine, ecology, quality control, and the like. One class of methods commonly referred to as immunoassays is dependent upon the use of a compound or receptor which specifically binds to another compound having a particular spatial and polar organization. The compound and its receptor form a homologous pair, referred to as ligand and receptor, where the receptor is normally antibody. One of the members of the homologous pair is bound to a label which is capable of providing a detectible signal.

The category of immunoassays may be further broken down into what is referred to as heterogeneous and homogeneous. The heterogeneous techniques are dependent upon separating associations or complexes of the homologous pair from members of the pair which are not associated. Since the complexes will substantially differ in molecular weight from the dissociated members, techniques such as centrifugation can be used to separate the associated from the dissociated members. One can then measure the label either in the phase containing the dissociated members or the phase containing the associated members. For the most part the labels which have found use in the heterogeneous methods are radiolabels, enzymes, and fluorescent molecules.

An alternative to physical separation is to bind one of the members of the homologous pair to a solid support, which may or may not absorb the aqueous medium. The solid support can then provide for the separation since the complexed or associated ligand and receptor is bound to the solid support. This allows for relatively easy separation between the aqueous assay medium and the solid support.

The homogeneous methods rely on the formation of complexes to modulate the signal obtained from the label. The dissociated conjugated label provides for a different level of signal from the associated conjugated label with its receptor. For example, where the ligand is conjugated to a stable free radical, the association of the conjugate with its homologous receptor results in a substantial flattening of the esr peaks. With enzymes as labels to which ligands have been conjugated, the binding of receptor to the ligands can result in steric inhibition of the approach of substrate to the active site of the enzyme or allosteric modification of enzyme activity. The presence of ligand in the assay medium reduces the amount of available receptor for binding to the label conjugate and thus affects the amount of the label conjugate which becomes associated with receptor. Therefore, by measurement of the signal from the label, one can relate the level of signal to the amount of ligand in the assay medium.

An alternative to employing the receptor to directly affect the signal by its bulk is the opportunity to bring together two labels which interact. Where a ligand is polyepitopic or a polyepitopic ligand is formed from monoepitopic ligands, the opportunity exists to allow for receptors which are labeled differently to be brought together when bound to the ligand or to have ligand with one label and receptor with a different label, which when the ligand and receptor are associated bring the labels into close spatial proximity. Where the different labels interact to affect the amount of signal observed, the associated ligand and receptor will provide for a different signal level from the dissociated labeled receptor.

This technique has been employed with chromophores which are related by one of the chromophores fluorescing at a wavelength of an energy which is accepted by the other chromophore, which acts as a quencher. Also, by employing two different enzymes, where the product of one enzyme is the substrate of the other enzyme, one can observe an enhanced turnover in the complex, as compared to the dissociated label.

The focus of effort in the homogeneous immunoassay area has been directed to either employ the properties of the complex to modulate the signal or to provide for the complex to bring together in close spatial proximity different labels which are related and provide for different degrees of interaction in relation to their distance from each other.

In developing immunoassays, there are many considerations, not the least of which is sensitivity. For measuring extremely small amounts of a ligand, it is either necessary to have a label which is detected at very low levels with high accuracy or to provide for a plurality of events associated with an individual ligand. Another consideration is interference by the foreign materials present and the degree to which the interference can be minimized or removed.

Another problem associated with immunoassays is labeling, particularly where the ligand or receptor is impure. The background resulting from conjugation of the label to compounds other than those of the homologous pair must be maintained at a minimum in order to obtain a satisfactorily sensitive assay. Other considerations include simplicity of protocol, ease of measurement, reproducibility, sensitivity to extraneous factors and the like.

2. Description of the Prior Art

Engasser and Horvath, Applied Biochem. Bioengineering, Vol. 1, 127 (1976) Academic Press, report the kinetic and diffusion effects on the immobilization of enzymes. U.S. Pat. No. 3,817,837 describes a homogeneous enzyme immunoassay. U.S. Pat. No. 3,996,345 describes a homogeneous immunoassay employing two chromophores related by being a fluorescer and a quencher. Copending application Ser. No. 893,650, filed Apr. 5, 1978, now U.S. Pat. No. 4,233,402, describes a technique employing a plurality of enzymes, where the substrate of one enzyme is the product of the other enzyme. Copending application Ser. No. 815,636, U.S. Pat. No. 4,160,645, filed July 14, 1977, now U.S. Pat. No. 4,160,645, describes a homogeneous immunoassay employing a non-enzymatic catalyst as a label. Co-pending application Ser. No. 906,514, now U.S. Pat. No. 4,193,983, filed May 16, 1978, describes a labeled liquid discontinuous phase for use in immunoassays. Application Ser. No. 667,996, abandoned, filed Mar. 18, 1976, describes a homogeneous immunoassay employing as a label an enzyme substrate. See also U.S. Pat. No. 3,853,987, which discloses particles to which are conjugated radioactive and fluorescent labels and antibodies. See also U.S. Pat. No. 4,001,400.

SUMMARY OF THE INVENTION

Methods and compositions are provided for the determination of an analyte which is a member of a specific binding pair—ligand and homologous receptor—where no separation or segregation is required for the determination. The method does not rely on a bulk effect where one observes the sum of the signal from the labels of associated members, but rather relies on an enhancement or diminution of the signal as a result of association. The method employs a substantially uniformly dispersed discontinuous phase of discrete solid (includes solvent swelled) particles (beads) in an aqueous assay medium. The particles are labeled with one of the members of the specific binding pair.

The particles create a physical or chemical environment distinctively different from the continuous aqueous phase. A signal producing system is provided which produces a substantially different level of detectible signal depending upon whether the signal producing system operates in the solid or liquid aqueous phase. By causing the distribution between the solid and liquid phase of the signal producing system to be related to the amount of analyte in the assay medium, the observed signal will be a function of the amount of analyte in the assay medium.

Conjugates to particles are provided for use in the method, as well as reagent compositions and kits. Also, specific compounds are provided as special substrates.

DESCRIPTION OF THE SPECIFIC EMBODIMENTS

A method is provided for determining low concentrations of organic compounds in a wide variety of media, particularly having physiological activity, either being naturally present in physiological fluids, or administered to vertebrates. The method employs as an assay medium a continuous liquid aqueous phase and a discontinous solid phase comprised of discrete small particles having relatively slow settling rates and being capable of providing an environment different from the environment of the continuous phase.

The particles are large discrete solid beads providing an environment for a label which may be distinguished from the environment of the bulk solution, preferably porous, providing channels or surface indentations of substantial depth where the liquid environment in the channel or indentation is significantly affected by the substantially encompassing solid phase. A signal producing system is provided, where the signal producing system, in whole or in part, is partitioned between the two phases in relation to the amount of analyte present in the assay medium. Since the observed signal will be substantially different depending upon the degree to which the signal producing system is partitioned between the liquid and the solid phase, the measured signal will reflect the amount of analyte in the assay medium.

The analyte will be a member of a specific binding pair consisting of the ligand and its homologous receptor. The solid phase particles or beads will be bound, directly or indirectly, covalently or non-covalently to one of the members of the specific binding pair. There is an exception where a specific type of receptor to a specific ligand is the analyte, three specific binding components are required, viz receptor, antireceptor or ligand, which may be bound to the particle, and ligand or antireceptor respectively, employed for other labeling. Thus receptor as an analyte allows for a number of alternative conjugates. In addition, one of the members of the signal producing system will be bound or become bound to the reciprocal member of the specific binding pair. By appropriate choice of specific binding pair conjugates, the amount of signal producing member bound to the particle can be related to the amount of analyte in the assay medium.

In carrying out the method, one combines the analyte containing sample, the labeled particles, the labeled specific binding pair member, as well as any additional reagents and determines the signal from the assay medium. By comparing the observed signal with a signal obtained from an assay medium having a known amount of analyte, one can qualitatively or quantitatively determine the analyte of interest. One can use the properties of the discrete particles in a number of different ways. Arbitrarily will be divided into two categories: (1) diffusion; and (2) physical effects;

By appropriate choice of porous particles, one can affect the rate at which a molecule or molecular assembly moves through the volume of the liquid phase adjacent to the solid particle surface. The effect of the steric bulk and narrow channels of the particles is to reduce the rate of migration of a molecule or molecular assembly toward and away from the particle surfaces, as compared to the rate of migration in the bulk solution, by virtue of physical constraint, and the like. Thus, one can create a substantial concentration gradient between the bulk liquid aqueous phase and the liquid portion adjacent the solid phase surface. A signal producing system which is sensitive to the concentration of a species will give substantially different signal levels in the bulk liquid phase as compared to the solid phase.

By having two members of the signal producing system which cooperate, that is, one member provides a compound which interacts with the second member, one can greatly enhance the localized concentration of the compound in the solid phase as compared to the bulk liquid phase. In these situations, the particle would not only be labeled with a member of the specific binding pair, but also a member of the signal producing system.

The second effect is a physical effect as a result of the chemical nature of the particle. The physical effect can be observed as pH, spectroscopic properties, and the like. In effect, the environment created by the particle surfaces, particularly in the channels or pores, for a molecule is substantially different from the environment in the bulk solution. Where the signal producing member is sensitive to its environment, there will be a substantially different signal depending upon whether the signal producing member is in the solid phase or in the bulk solution. For example, the activity of an enzyme is pH dependent. By appropriate choice of buffer and an ion exchange resin, the pH at the surface of the solid phase can be distinctively different from the pH in the bulk solution. The enzymatic activity would therefore vary depending upon the partitioning of the enzyme between the two phases.

The polarity between the particle and the bulk solution can be greatly varied by employing a hydrophobic particle. The hydrophobic character could activate or deactivate an enzyme or chromogen e.g. fluorescer.

The spectroscopic effect can be exemplified by employing opaque, transparent or partially transparent (within a limited wavelength range) particles. One could therefore control the light that entered or exited from the particle. Alternatively, phosphorescent labeled (includes embedded) particles could be employed or particles having labels capable of energy transfer to a chromogen.

In performing the subject method, there will be at least two reagents: the particle conjugate; and the specific binding pair member conjugate. These conjugates will vary depending upon the nature of the analyte, the nature of the signal producing system, and the nature of the particle. In addition, by covalently bonding molecules, particularly enzymes to the particle, one can create a concentration gradient, where the bulk solution has a relatively low concentration of the particular compound or enzyme product. These molecules can be part of the signal producing system or merely provide an environment which affects the signal producing system.

DEFINITIONS

Analyte—the compound or composition to be measured, which may be a ligand, which is mono- or polyepitopic, antigenic or haptenic, a single or plurality of compounds which share at least one common epitopic site or a receptor.

Specific binding pair—two different molecules, where one of the molecules has an area on the surface or in a cavity which specifically binds to a particular spatial and polar organization of the other molecule. The members of the specific binding pair are referred to as ligand and receptor (antiligand).

Ligand—any organic compound for which a receptor naturally exists or can be prepared.

Receptor (antiligand)—any compound or composition capable of recognizing a particular spatial and polar organization of a molecule i.e. epitopic site. Illustrative receptors include naturally occurring receptors, e.g. thyroxine binding globulin, antibodies, enzymes, Fab fragments, lectins and the like.

Ligand Analog—a modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand-analog)—a plurality of ligands or ligand analogs joined together covalently, normally to a hub nucleus. The hub nucleus is a polyfunctional material, normally polymeric, usually having a plurality of functional groups e.g. hydroxy, amino, mercapto, ethylenic, etc. as sites for linking. The hub nucleus may be water soluble or insoluble, preferably water soluble, and will normally be at least about 35,000 molecular weight and may be 10 million or more molecular weight, but usually under 600,000, more usually under 300,000. Illustrative hub nuclei include polysaccharides, polypeptides, including proteins, nucleic acids, ion exchange resins and the like. Water insoluble hub nuclei can be the same as those indicated for the particle.

Particle (solid phase)—the particle is a discrete solid particle, which may be swelled or remain unswelled by the liquid phase, and composed of a wide variety of both hydrophobic and hydrophilic materials. The particles will be solid, hollow or porous, having a substantially smooth or irregular surface, having a primarily concave or convex surface, preferably being porous and having channels or indentations, which can be widely varied as to the size of molecule or assembly which is excluded, defining an environment different from the medium in which the particles are dispersed. The particles will be readily dispersible in an aqueous medium, and either polyfunctionalized or capable of polyfunctionalization for linking to other molecules. Depending on the signal producing system, the particles may be substantially transparent to light in a substantial wavelength range between 300 and 800 nm, preferably through the range or be opaque over the entire ultraviolet and visible range.

Signal producing system—the signal producing system may have one or more components, at least one component being conjugated to a specific binding pair member. The signal producing system produces a measurable signal which is detectible by external means, usually the measurement of electromagnetic radiation, and depending on the system employed, the level of signal will vary to the extent the signal producing system is in the environment of the solid phase particles. For the most part, the signal producing system will involve enzymes and chromophores, where chromophores include dyes which absorb light in the ultraviolet or visible region, phosphors, fluorescers, and chemiluminescers. While for the most part, the signal is conveniently the absorption or emission of electromagnetic radiation, usually in the ultraviolet or visible range, electrochemical changes, thermal changes, nephelometric changes, and the like may also find application.

Label—the label may be any molecule conjugated to another molecule and is arbitrarily chosen as to which molecule is the label. In the subject invention, the labels will be the specific binding pair molecule that is conjugated to the particle or a molecule which is part of the signal producing system that is conjugated to a member of the specific binding pair or to a particle.

Particle conjugate—the particle to which is bound, directly or indirectly a member of the specific binding pair, and, as appropriate one or more members of the signal producing system. A substantial proportion of the labels conjugated to the particle will be influenced by the particle surface, usually within the channels and pores of the particle when these are present, so that where the signal producing member is bound to the particle, there is a property of the conjugate which differentiates the signal obtained from the particle as compared to the signal obtained from the bulk solution.

Binding pair label—a member of the specific binding pair employed for binding its homologous member to the particle directly bonded to the particle.

Signal label—a member of the signal producing system which is directly or indirectly (through the binding of a specific binding pair) bonded to a binding pair member or to the particle.

Binding pair member conjugate or signal label conjugate—the conjugate of the binding pair member with a member of the signal producing system (signal label).

Labeled ligand—the conjugate of the ligand member of the specific binding pair with a member of the signal producing system, either covalently or noncovalently bound, when covalently joined, either joined by a bond, linking group, or hub nucleus. The labeled ligand may have one or more ligands (includes ligand analogs) or one or more labels or a plurality of both, the latter being referred to as poly(ligand analog)-polylabel.

Labeled receptor—the conjugate of receptor with a member of the signal producing system, where the two are bound either covalently or non-covalently, usually covalently by a linking group, where there may be one or more receptors bound to the label, but usually one or more labels bound to the receptor.

Macromolecular reagent—a reagent capable of interacting with a member of the signal producing system to modulate the signal and at least in part sterically excluded from interacting with a member of the signal producing system in the environment of the particle conjugate through steric constraints or reduced rates of diffusion. The reagent will usually have a minimum molecular weight of at least about 20,000, more usually at least about 40,000 and preferably at least about 100,000. The reagent may naturally have such molecular weight or the active compound linked to a hub nucleus to provide the desired molecular weight.

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample, which may have been subject to prior treatment, the particle conjugate, the binding pair member conjugate, all of the materials required for the signal producing system for producing a detectible signal, as well as members of the specific binding pair or their analogs, as required.

The presence of ligand or its homologous receptor (antiligand) in the unknown will affect the partition of the signal producing system between the particle or solid phase and the bulk solution in the assay medium.

In carrying out the assay, an aqueous medium will normally be employed. Other polar solvents may also be included, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particle buffer employed is not critical to this invention but in individual assays, one buffer may be preferred over another.

Moderate temperatures are normally employed for carrying out the assay and usually constant temperatures during the period of the measurement, particularly for rate determinations. The temperatures for the determination will generally range from about 10°–50° C., more usually from about 15°–40° C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-qualitative or quantitative, the particular detection technique and the concentration of the analyte of interest will normally determine the concentration of the other reagents.

While the concentrations of the various reagents in the assay medium will generally be determined by the concentration range of interest and of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of analyte and usually not more than about 1,000 times the maximum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding.

Depending upon the particular signal producing system, as well as the manner in which the specific binding pair members are employed, the amount of the various conjugates can be varied quite widely. For example, one could have very large excesses of the binding pair label in the particle conjugate, by first allowing the binding pair member conjugate to react with the unknown, followed by combining with the particle conjugate. Where a competition mode was employed, in that the particle conjugate and the binding pair member conjugate are added to the unknown simultaneously, large excesses of the binding pair label might reduce the sensitivity of the assay. Therefore, as indicated previously, by employing various concentrations of the various reagents with analyte at concentrations in the range of interest, one would obtain ratios which would optimize the assay response.

The order of addition of the various reagents may vary widely, depending upon the particular labels, the compound to which the label is conjugated, the nature of the conjugates, the nature of the analyte, and the relative concentrations of the analyte and reagents. Also affecting the order of addition is whether an equilibrium mode or rate mode is employed in the determination.

Since with many receptors, the association of the specific binding pair members is almost irreversible during the time period of the assay, one will normally avoid combining the particle conjugate with the signal label conjugate, prior to the addition of the analyte, where the two conjugates are reciprocal members of the specific binding pair. By contrast, where the two conjugates have the same member of the specific binding pair, one could combine them prior to introduction of the unknown sample into the assay medium. Regardless of the nature of the analyte, all the reagents can be added simultaneously and either a rate or equilibrium determination made.

One or more incubation steps may be involved in preparing the assay medium. For example, it may be desirable to incubate an antigen analyte with labeled receptor. In addition, it may be desirable to have a second incubation after addition of the particle conjugate. Whether to employ an incubation period and the length of the incubation period, will depend to a substantial degree on the mode of determination—rate or equilibrium—and the rate of binding of the receptor to the ligand. Usually, incubation steps will vary from about 0.5 min to 6 hrs, more usually from about 5 min to 1 hr. Incubation temperatures will generally range from about 4° to 50° C., more usually from about 15° to 37° C.

After the reagents are combined, the signal will then be determined. The method of determination may be the observation of electromagnetic radiation, particularly ultraviolet and visible light, either absorption or emission, colorimetric, electrochemical, nephelometric, or the like. Desirably, the signal will be read as electromagnetic radiation in the ultraviolet or visible region, particularly from about 250 to 750 nm, usually from about 350 to 650 nm.

The temperature at which the signal is observed will generally range from about 10° to 50° C., more usually from about 15° to 40° C.

Standard assay media can be prepared which have known amounts of the analyte. The observed signal for the standard assay media may then be plotted, so as to relate concentration to signal. Once a standard curve has been established, a signal may be directly related to the concentration of the analyte.

The time for measuring the signal will vary depending on whether a rate or equilibrium mode is used, the sensitivity required, the nature of the signal producing system and the like. For rate mode the times between readings will generally vary from about 5 sec to 6 hrs, usually about 10 sec to 1 hr. For the equilibrium mode, after a steady state is achieved, a single reading may be sufficient or two readings over any convenient time interval may suffice.

The variety of effects which may be achieved by the particles, allows for great versatility in designing reagents for the assay. The following table is illustrative of the more obvious variations permitted with signal producing systems employing one or more enzymes. The list is not intended to be exhaustive, but rather illustrative of the simpler and more accessible signal producing systems and reagent combinations. In addition, it should be appreciated, that different combinations will be preferred depending upon the required sensitivity of the assay, the nature of the analyte, as well as the source of the unknown sample.

TABLE I

| Analtye[1] | Particle Conjugate[2] | Binding Pair Member Conjugate[3] | Signal Producing System Reagents[4] |
|---|---|---|---|
| Ag | P-Ag | Ab-Enz | a, b or c |
| Ag | P-Ab | Ab-Enz | a, b or c |
| Ag | P-Ab | Ag-Enz | a, b or c |
| Ag | P-Ag | Ab-Enz$_1$-Enz$_2$ | a |
| Ag | P-Ab | Ab-Enz$_1$-Enz$_2$ | a |
| Ag | P-Ab | Ag-Enz$_1$-Enz$_2$ | a |
| Ag | P-Ag | Ab-Enz$_1$, Ab-Enz$_2$ | a |
| Ag | P-Ab | Ab-Enz$_1$, Ab-Enz$_2$ | a |
| Ag | P-Ab | Ag-Enz$_1$, Ag-Enz$_2$ | a |
| Ag | P-Ag-Enz$_1$ | Ab-Enz$_2$ | a |
| Ag | P-Ab-Enz$_1$ | Ab-Enz$_2$ | a |
| Ag | P-Ab-Enz$_1$ | Ag-Enz$_2$ | a |
| Ag | P-Ag | Ab-F | e, f |
| Ag | P-Ab | Ab-F | e, f |
| Ag | P-Ag-F | Ab-Enz | d |
| Ag | P-Ab-F | Ab-Enz | d |
| Ag | P-Ab-F | Ag-Enz | d |
| Ag | P-Ag | Ab-F | e, f |
| Ab | P-Ab | Ab-F | e, f |
| Ab | P-Ab-F | Ag-Enz | d |
| Ab | P-Ag | Ab-Enz | a, b or c |

TABLE I-continued

| Analtye[1] | Particle Conjugate[2] | Binding Pair Member Conjugate[3] | Signal Producing System Reagents[4] |
|---|---|---|---|
| Ab | P-Ab | Ag-Enz | a, b or c |

[1]Ag-ligand
Ab-receptor, usually polyvalent
[2]P-Ag particle conjugated with antigen
P-Ab particle conjugated with antibody
P-Ag-Enz$_1$ particle conjugated with antigen and enzyme
P-Ab-Enz$_1$ particle conjugated with antibody and enzyme
P-Ag-F particle conjugated with antigen and fluorescer
P-Ab-F particle conjugated with antibody and fluorescer
[3]Ab-Enz antibody conjugated with enzyme
Ag-Enz antigen conjugated with enzyme
Ab-Enz$_1$-Enz$_2$ antibody conjugated with two different enzymes where the product of one is the substrate of the other
Ag-Enz$_1$-Enz$_2$ antigen conjugated with two different enzymes where the product of one is the substrate of the other
Ab-Enz$_1$, Ab-Enz$_2$ antibodies to the same ligand, a portion of which is conjugated to one enzyme and a portion conjugated to a different enzyme which employs the product of the first enzyme as its substrate.
Ag-Enz$_1$, Ag-Enz$_2$ antigen, where portions are bonded to different enzymes, the substrate of one enzyme being the product of the other enzyme
Ab-Enz$_2$ antibody conjugated with an enzyme related to Enz$_1$, in that the substrate of one of the enzymes is the product of the other enzyme
Ag-Enz$_2$ antigen conjugated with an enzyme related to Enz$_1$, in that the substrate of one of the enzymes is the product of the other enzyme
Ab-F antibody conjugated with a fluorescing chromophore (F)
[4]a-small substrates
b-large substrate as compared to particle pore size
c-small substrate, large inhibitor as compared to particle pore size
d-compound which reacts with enzyme (Enz) to chemiluminesce and transfer energy to the fluorescer which fluoresces
e-antifluorescer
f-particle environment affects fluorescence Rather than unduly extending the table, the situation with antibody or receptor as an analyte is illustrated in comparison to the situation with antigen as analyte. Generally, where antibody is the analyte, in each of the illustrative examples, one need merely replace the symbol for antigen with antibody and the symbol for antibody with antigen.

The ligand may be mono- or polyepitopic. In most situations this difference will not affect the manner in which the assay is performed. Where the analyte is a ligand, the specific binding pair member in the particle conjugate may be either ligand or receptor. The binding pair member conjugate (containing the signal label) can have either ligand or receptor. However, where both the particle conjugate and the binding pair member conjugate have receptor, the ligand must be polyepitopic or made so by employing a poly(ligand analog) as an additional reagent. That is, a sandwich technique is employed where the ligand binds to the particle conjugate and provides epitopic sites for binding of the binding pair member conjugate to the particle conjugate.

Where the receptor is the analyte, the particle conjugate and the binding pair member conjugate may have the same or different members of the specific binding pair, with the proviso that receptor is polyvalent when ligand is involved in both conjugates.

In the event that the analyte and the two conjugates all have or contain the same member of the specific binding pair, then the homologous member must be added and it must be provided in polyepitopic form, either as an antibody, or a polyvalent receptor, where it is a receptor or as polyhapten (poly(ligand analog)), where it is a ligand.

Where a single component of the signal producing system is employed as the label, one or more properties of the particle may be involved in affecting the level of signal. Where two enzymes are involved, or one enzyme and a combination of related chromophores, while other properties of the particle may have some effect, the primary effect of the particle will usually be on the rate of diffusion of an enzyme product. Similarly, where a large substrate or a large inhibitor or quencher is involved, the primary effect of the particle is on the rate of diffusion of the substrate, inhibitor, or quencher to the signal label conjugate that becomes bound to the particle.

The subject method also lends itself to the simultaneous determination of the presence of a plurality e.g. two or more, analytes, where the signal producing system has at least an equal number of members which interact in an additive or successive manner. The situation can be illustrated for two antigen analytes. By binding antibodies to the antigen analytes to the particle and having antibody for one antigen analyte conjugated to $Enz_1$ and antibody for the other antigen analyte conjugated to $Enz_2$, $Enz_1$ and $Enz_2$ are enzymes where the substrate of $Enz_2$ is the product of $Enz_1$, and measuring for the product of $Enz_2$, there will be an enhancement in the production of $Enz_2$ product when both enzymes are bound to the particle through the intermediacy of the antigens. The two enzymes can only be bound to the particle when both antigens are present in the assay medium. One can reverse the situation with polyvalent receptor analytes or employ different combinations.

This technique can also be considered from the standpoint of having the second analyte, the signal label and associated reagents as part of the signal producing system, which cooperates with the members of the signal producing system associated with the first analyte to produce a signal. However, it should be appreciated that this application evidences the presence of both analytes, without determining the individual concentration of the two analytes.

Where the primary effect of the particle is to provide an environment for the signal producing system distinctively different from the bulk solution, consideration will have to be given, not only to the effect of the different environment on the signal system, but also on the association of the specific binding pair. For the most part, the degree of association or binding constant will not vary significantly over relatively broad areas of pH, and the like. Therefore, while the effect of the environment of the particle on the association of the specific binding pair will not significantly affect the results, this effect should not be ignored.

MATERIALS

The components employed in the assay will be the particle conjugate, the binding pair member conjugate(s) and the reagents which are the remaining members of the signal producing system, as well as the analyte, and, as appropriate, poly(ligand analog), and polyvalent receptor. Employed in the preparation of the reagents, will be particles or beads, and members of the signal producing system.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:

protamines
histones
albumins
globulins
scleroproteins
phosphoproteins
mucoproteins
chromoproteins
lipoproteins
nucleoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
   $\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I β₂-glycoprotein II
Immunoglobulin G
  (IgG) or γG-globulin
Mol. formula:
  $\gamma_2\kappa_2$ or $\gamma_2\lambda_2$
Immunoglobulin A (IgA)
  or γA-globulin
Mol. formula:
  $(\alpha_2\kappa_2)^n$ or $(\alpha_2\lambda_2)^n$
Immunoglobulin M
  (IgM) or γM-globulin
Mol. formula:
  $(\mu_2\kappa_2)^5$ or $(\mu_2\lambda_2)^5$
Immunoglobulin D(IgD)
  or γD-Globulin (γD)
Mol. formula:
  $(\delta_2\kappa_2)$ or $(\delta_2\lambda_2)$
Immunoglobulin E (IgE)
  or γE-Globulin (γE)
Mol. formula:
  $(\epsilon_2\kappa_2)$ or $(\epsilon_2\lambda_2)$
Free K and γ light chains
  Complement factors:
C'1
  C'1q
  C'1r
  C'1s
C'2
C'3
  β₁A
  α₂D
C'4
C'5
C'6
C'7
C'8
C'9

Important blood clotting factors include:

| BLOOD CLOTTING FACTORS | |
| --- | --- |
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stablilizing factor |

Important protein hormones include:

Peptide and Protein Hormones

Parathyroid hormone (parathromone)
Thyrocalcitonin
Insulin
Glucagon
Relaxin
Erythropoietin
Melanotropin (melanocyte-stimulating hormone; intermedin)
Somatotropin (growth hormone)
Corticotropin (adrenocorticotropic hormone)
Thyrotropin
Follicle-stimulating hormone
Luteinizing hormone (interstitial cell-stimulating hormone)
Luteomammotropic hormone (luteotropin, prolactin)
Gonadotropin (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
CRF, LRF, TRF, Somatotropin-RF,
GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
| --- | --- |
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |
| Shigella dysenteriae Shigella flexneri | Polysaccharide |
| Shigella sonnei | Crude,polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
   Corynebacterium diptheriae
Pneumococci
   Diplococcus pneumoniae
Streptococci
   Streptococcus pyogenes
   Streptococcus salivarus
Staphylococci
   Staphylococcus aureus
   Staphylococcus albus
Neisseriae
   Neisseria meningitidis
   Neisseria gonorrheae
Enterobacteriaciae
   Escherichia coli
   Aerobacter aerogenes    } The coliform bacteria
   Klebsiella pneumoniae
   Salmonella typhosa
   Salmonella choleraesuis    } The Salmonellae
   Salmonella typhimurium
   Shigella dysenteriae
   Shigella schmitzii
   Shigella arabinotarda    } The Shigella
   Shigella flexneri
   Shigella boydii
   Shigella Sonnei
Other enteric bacilli
   Proteus vulgaris
   Proteus mirabilis    } Proteus species
   Proteus morgani
   Pseudomonas aeruginosa
   Alcaligenes faecalis
   Vibrio cholerae
Hemophilus-Bordetella group
   Hemophilus influenzae,    H. ducreyi
         H. hemophilus
         H. aegypticus
         H. parainfluenzae
   Bordetella pertussis
Pasteurellae
   Pasteurella pestis
   Pasteurella tulareusis
Brucellae
   Brucella melitensis
   Brucella abortus
   Brucella suis
Aerobic Spore-forming Bacilli
   Bacillus anthracis
   Bacillus subtilis
   Bacillus megaterium
   Bacillus cereus
Anaerobic Spore-forming Bacilli
   Clostridium botulinum
   Clostridium tetani
   Clostridium perfringens
   Clostridium novyi
   Clostridium septicum
   Clostridium histolyticum
   Clostridium tertium
   Clostridium bifermentans
   Clostridium sporogenes
Mycobacteria
   Mycobacterium tuberculosis hominis
   Mycobacterium bovis
   Mycobacterium avium
   Mycobacterium leprae
   Mycobacterium paratuberculosis
Actinomycetes (fungus-like bacteria)
   Actinomyces israelii
   Actinomyces bovis
   Actinomyces naeslundii
   Nocardia asteroides
   Nocardia brasiliensis
The Spirochetes
   Treponema pallidum    Spirillum minus
   Treponema pertenue    Streptobacillus moniliformis
   Treponema carateum
   Borrelia recurrentis -continued Leptospira icterohemorrhagiae
   Leptospira canicola
Mycoplasmas
   Mycoplasma pneumoniae
Other pathogens
   Listeria monocytogenes
   Erysipelothrix rhusiopathiae
   Streptobacillus moniliformis
   Donvania granulomatis
   Bartonella bacilliformis
Rickettsiae (bacteria-like parasites)
   Rickettsia prowazekii
   Rickettsia mooseri
   Rickettsia rickettsii
   Rickettsia conori
   Rickettsia australis
   Rickettsia sibiricus
   Rickettsia akari
   Rickettsia tsutsugamushi
   Rickettsia burnetii
   Rickettsia quintana
Chlamydia (unclassifiable parasites bacterial/viral)
   Chlamydia agents (naming uncertain)
Fungi
   Cryptococcus neoformans
   Blastomyces dermatidis
   Histoplasma capsulatum
   Coccidioides immitis
   Paracoccidioides brasiliensis
   Candida albicans
   Aspergillus fumigatus
   Mucor corymbifer (Absidia corymbifera)
   Rhizopus oryzae
   Rhizopus arrhizus    } Phycomycetes
   Rhizopus nigricans
   Sporotrichum schenkii
   Fonsecaea pedrosoi
   Fonsecaea compacta
   Fonsecaea dermatitidis
   Cladosporium carrionii
   Phialophora verrucosa
   Aspergillus nidulans
   Madurella mycetomi
   Madurella grisea
   Alleschoria boydii
   Phialophora jeanselmei
   Microsporum gypseum
   Trichophyton mentagrophytes
   Keratinomyces ajelloi
   Microsporum canis
   Trichophyton rubrum
   Microsporum andouini
Viruses
   Adenoviruses
   Herpes viruses
      Herpes simplex
      Varicella (Chicken pox)
      Herpes Zoster (Shingles)
      Virus B
      Cytomegalovirus
   Pox Viruses
      Variola (smallpox)
      Vaccinia
      Poxvirus bovis
      Paravaccinia
      Molluscum contagiosum
   Picornaviruses
      Poliovirus
      Coxsackievirus
      Echoviruses
      Rhinoviruses
   Myxoviruses
      Influenza (A, B, and C)
      Parainfluenza (1-4)
      Mumps Virus
      Newcastle Disease Virus
      Measles Virus
      Rinderpest Virus
      Canine Distemper Virus -continued Respiratory Syncytial Virus
Rubella Virus
Arboviruses
   Eastern Equine Eucephalitis Virus
   Western Equine Eucephalitis Virus
   Sindbis Virus
   Chikugunya Virus
   Semliki Forest Virus
   Mayora Virus
   St. Louis Encephalitis Virus
   California Encephalitis Virus
   Colorado Tick Fever Virus
   Yellow Fever Virus
   Dengue Virus
Reoviruses
   Reovirus Types 1-3
Hepatitis
   Hepatitis A Virus
   Hepatitis B Virus
Tumor Viruses
   Rauscher Leukemia Virus
   Gross Virus
   Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand Analog

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1-20 atoms other than hydrogen, which are carbon, oxygen, sulfur, nitrogen, and halogen of atomic number 17-35. The functionalities which are involved include carbonyl, both oxo and non-oxo, active halogen, diazo, mercapto, ethylene, particularly activated ethylene, amino, and the like. The number of heteroatoms will generally range from about 0-6, more usually from about 1-6, and preferably from about 1-4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1–10, more usually from about 1–6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analgous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or as mixed anhydrides with carbonate monesters or as active carboxylic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alkylamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl groups, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

Signal Producing System

The signal producing system will have at least one member, usually two members, and will provide a detectible signal in the assay medium. The level of the observed signal will be influenced by the partitioning of the signal producing system between the particle and the bulk solution, the solid environment of the particle and the liquid environment of the aqueous medium. Therefore, the properties of the particle must affect the level of the signal observed as compared to the signal which would be observed from the signal producing system in the bulk solution in the absence of the particles. In addition, it is desirable that the signal producing system provide for several measurable events in response to the binding between the members of a single specific binding pair (amplification).

The signal producing systems of primary interest will be those involving catalysts, either enzymatic or nonenzymatic, particularly enzymatic, or chromophores which absorb or emit light, particularly fluorescers and chemiluminescers, as well as combinations of the two types of systems. However, while the aforementioned labels will be more commonly employed, other types of labels may also find use, such as stable free radicals, involving their formation or destruction, labels for potentiometric determination, and the like.

The first type of system to be considered will be those involving enzymes.

Enzymes

As depicted in Table 1, a signal producing system may involve a single enzyme. By employing an enzyme where the effect of the particle environment influences the turnover rate, either increasing or decreasing the turnover rate, the observed signal will vary with the partitioning of the enzyme between the particles or solid phase and the bulk solution. Since enzymes are sensitive to pH, hydrophobic surfaces, ionic strength, and the like, particularly pH, by providing for appropriate particles, the enzymatic turnover rate can be modulated.

In choosing an enzyme, in addition to the effect of the particle on the enzyme turnover rate, other considerations will also affect the choice of enzyme. These considerations include the stability of the enzyme, the desirability of a high turnover rate, the sensitivity of the rate to variations in the physical environment, the nature of the substrate(s) and product(s), particularly the ability to measure the substrate or product, preferably the product, the availability of the enzyme, the effect of conjugation of the enzyme on the enzyme's properties, the effect on enzyme activity of materials which may be encountered in the sample solutions, the molecular weight of the enzyme, and the like.

The following are categories of enzymes as set forth in accordance with the classification of the International Union of Biochemistry.

TABLE II

1. Oxiodoreductases
    1.1  Acting on the CH—OH group of donors
        1.1.1  With NAD or NADP as acceptor
        1.1.2  58 a cytochrome as an acceptor
        1.1.3  With $O_2$ as acceptor
        1.1.99  With other acceptors
    1.2  Acting on the aldehyde or keto group of donors
        1.2.1  With NAD or NADP as acceptor
        1.2.2  With a cytochrome as an acceptor
        1.2.3  With $O_2$ as acceptor
        1.2.4  With lipoate as acceptor
        1.2.99  With other acceptors
    1.3  Acting on the CH—CH group of donors
        1.3.1  With NAD or NADP as acceptors
        1.3.2  With a cytochrome as an acceptor
        1.3.3  With $O_2$ as acceptor
        1.3.99  With other acceptors
    1.4  Acting on the CH—$NH_2$ group of donors
        1.4.1  With NAD or NADP as acceptor
        1.4.3  With $O_2$ as acceptor
    1.5  Acting on the C—NH group of donors
        1.5.1  With NAD or NADP as acceptor
        1.5.3  With $O_2$ as acceptor
    1.6  Acting on reduced NAD or NADP as donor
        1.1.6  With NAD or NADP as acceptor
        1.6.2  With a cytochrome as an acceptor
        1.6.4  With a disulfide compound as acceptor
        1.6.5  With a quinone or related compound as acceptor
        1.6.6  With a nitrogenous group as acceptor
        1.6.99  With other acceptors
    1.7  Acting on other nitrogenous compounds as donors
        1.7.3  With $O_2$ as acceptor
        1.7.99  With other acceptors
    1.8  Acting on sulfur groups of donors
        1.8.1  0 With NAD or NADP as acceptor
        1.8.3  With $O_2$ as acceptor
        1.8.4  With a disulfide compound as acceptor
        1.8.5  With a quinone or related compound as acceptor
        1.8.6  With a nitrogenous group as acceptor
    1.9  acting on heme groups of donors
        1.9.3  With $O_2$ as acceptor
        1.9.6  With a nitrogenous group as acceptor
    1.10  Acting on diphenols and related substances as donors
        1.10.3 With $O_2$as acceptor
    1.11  Acting on $H_2O_2$ as acceptor
    1.12  Acting on hyrdrogen as donor
    1.13  Acting on single donors with incorporation of oxygen (oxygenases)

TABLE II-continued

| | | |
|---|---|---|
| 1.14 | Acting on paired donors with incorporation of oxygen into one donor (hydroxylases) | |
| | 1.14.1 | Using reduces NAD or NADP as one donor |
| | 1.14.2 | Using ascorbate as one donor |
| | 1.14.3 | Using reduced pteridine as one donor |
| 2. Transferases | | |
| | 2.1 | Transferring one-carbon groups |
| | | 2.1.1 Methyltransferases |
| | | 2.1.2 Hydroxymethyl-, formyl- and related transferases |
| | | 2.1.3 Carboxyl- and carbomoyltransferases |
| | | 2.1.4 Amidinotransferases |
| | 2.2 | Transferring aldehydic or ketonic residues |
| | 2.3 | Acyltransferases |
| | | 2.3.1 Acyltransferases |
| | | 2.3.2 Aminoacyltransferases |
| | 2.4 | Glycosyltransferases |
| | | 2.4.1 Hexosyltransferases |
| | | 2.4.2 Pentosyltransferases |
| | 2.5 | Transferring alkyl or related groups |
| | 2.6 | Transferring nitrogenous groups |
| | | 2.6.1 Aminotransferases |
| | | 2.6.3 Aximinotransferases |
| | 2.7 | Transferring phosphorus-containing groups |
| | | 2.7.1 Phosphotransferases with an alcohol group as acceptor |
| | | 2.7.2 Phosphotransferases with a carboxyl group as acceptor |
| | | 2.7.3 Phosphotranferases with a nitrogenous group as acceptor |
| | | 2.7.4 Phosphotransferases with a phospho-group as acceptor |
| | | 2.7.5 Phosphotransferases, apparently intramolecular |
| | | 2.7.6 Pyrophosphotransferases |
| | | 2.7.7 Nucleotidyltransferases |
| | | 2.7.8 Transferases for other substituted phospho-groups |
| | 2.8 | Transferring sulfur-containing groups |
| | | 2.8.1 Sulfurtransferases |
| | | 2.8.2 Sulfotransferases |
| | | 2.8.3 CoA-tranferases |
| 3. Hydrolases | | |
| | 3.1 | Acting on ester bonds |
| | | 3.1.1 Carboxylic ester hydrolases |
| | | 3.1.2 Thiolester hydrolases |
| | | 3.1.3 Phosphoric monoester hydrolases |
| | | 3.1.4 Phosphoric diester hydrolases |
| | | 3.1.5 Triphosphoric monoester hydrolases |
| | | 3.1.6 Sulfuric ester hydrolases |
| | 3.2 | Acting on glycosyl compounds |
| | | 3.2.1 Glycoside hydrolases |
| | | 3.2.2 Hydrolysing N-glycosyl compounds |
| | | 3.2.3 Hydrolizing S-glycosyl compounds |
| | 3.3 | Acting on ether bonds |
| | | 3.3.1 Thioether hydrolases |
| | 3.4 | Acting on peptide bonds (peptide hydrolases) |
| | | 3.4.1 α-Aminoacyl-peptide hydrolases |
| | | 3.4.2 Peptidyl-aminoacid hydrolases |
| | | 3.4.3. Dipeptide hyrolases |
| | | 3.4.4 Peptidyl-peptide hydrolases |
| | 3.5 | Acting on C—N bonds other than peptide bonds |
| | | 3.5.1 In linear amides |
| | | 3.5.2 In cyclic amides |
| | | 3.5.3 In linear amidines |
| | | 3.5.4 In cyclic amidines |
| | | 3.5.5 In cyanides |
| | | 3.5.99 In other compounds |
| | 3.6 | Acting on acid-anhydride bonds |
| | | 3.6.1 In phosphoryl-containing anhydrides |
| | 3.7 | Acting on C—C bonds |
| | | 3.7.1 In ketonic substances |
| | 3.8 | Acting on halide bonds |
| | | 3.8.1 in C-halide compounds |
| | | 3.8.2 In P-halide compounds |
| | 3.9 | Acting on P—N bonds |
| 4. Lyases | | |
| | 4.1 | Carbon-carbon lyases |
| | | 4.1.1 Carboxy-lyases |
| | | 4.1.2 Aldehyde-lyases |
| | | 4.1.3 Ketoacid-lyases |

TABLE II-continued

| | | |
|---|---|---|
| | 4.2 | Carbon-oxygen lyases |
| | | 4.2.1 Hydro-lyases |
| | | 4.2.99 Other carbon-oxygen lyases |
| | 4.3 | Carbon-nitrogen lyases |
| | | 4.3.1 Ammonia-lyases |
| | | 4.3.2 Amidine-lyases |
| | 4.4 | Carbon-sulfur lyases |
| | 4.5 | Carbon-halide lyases |
| | 4.99 | Other lyases |
| 5. Isomerases | | |
| | 5.1 | Racemases and epimerases |
| | | 5.1.1 Acting on amino acids and derivatives |
| | | 5.1.2 Acting on hydroxy acids and derivatives |
| | | 5.1.3. Acting on carbohydrates and derivatives |
| | | 5.1.99 Acting on other compounds |
| | 5.2 | Cis-trans isomerases |
| | 5.3 | Intramolecular oxidoreductases |
| | | 5.3.1 Interconverting aldoses and ketoses |
| | | 5.3.2 Interconverting keto and enol groups |
| | | 5.3.3. Transposing C=C bonds |
| | 5.4 | Intramolecular transferases |
| | | 5.4.1 Transferring acyl groups |
| | | 5.4.2 Transferring phosphoryl groups |
| | | 5.4.99 Transferring other groups |
| | 5.5 | Intramolecular lyases |
| | 5.99 | Other isomerases |
| 6. Ligases or Synthetases | | |
| | 6.1 | Forming C—O bonds |
| | | 6.1.1 Aminoacid-RNA ligases |
| | 6.2 | Forming C—S bonds |
| | | 6.2.1 Acid-thiol ligases |
| | 6.3 | Forming C—N bonds |
| | | 6.3.1 Acid-ammonia ligases (amide synthetases) |
| | | 6.3.2 Acid-aminoacid ligases (peptide synthetases) |
| | | 6.3.3 Cyclo-ligases |
| | | 6.3.4 Other C—N ligases |
| | | 6.3.5 C—N ligases with glutamine as N-donor |
| | 6.4 | Forming C—C bonds |

Of particular interest will be enzymes which are in Class 1. Oxidoreductases and Class 3 hydrolases, although enzymes of Class 2, Transferases, Class 4 Lyases and Class 5, Isomerases, can also be of interest in particular situations.

The following table has specific subclasses of enzymes and specific enzymes within the subclass which are of particular interest. Among the oxidoreductases, those involving NAD or NADP, oxygen or hydrogen peroxide are of particular interest. Among the hydrolases, those involving phosphate and glycosides are of particular interest.

TABLE III

1. Oxidoreductases
   1.1 Acting on the CH—OH group of donors
      1.1.1 With NAD or NADP as acceptor
         1. alcohol dehydrogenase
         6. glycerol dehydrogenase
         27. lactate dehydrogenase
         37. malate dehydrogenase
         49. glucose-6-phosphate dehydrogenase
      1.1.3 With $O_2$ as acceptor
         4. glucose oxidase
            galactose oxidase
   1.2 Acting on the aldehyde or keto group of donors
      1.2.1 With NAD or NADP as acceptor
         12. glyceraldehyde-3-phosphate dehydrogenase
      1.2.3 With $O_2$ as acceptor
         2. xanthine oxidase
            luciferase
   1.4 Acting on the CH—NH$_2$ group of donors
      1.4.3 With $O_2$ as acceptor
         2. L-amino acid oxidase

TABLE III-continued

3. D-amino acid oxidase
1.6 Acting on reduced NAD or NADP as donor
    1.6.99  With other acceptors
              diaphorase
1.7 Acting on other nitrogenous compounds as donors
    1.7.3  With $O_2$ as acceptor
           3. uricase
1.11 Acting on $H_2O_2$ as acceptor
    1.11.1
           6. catalase
           7. peroxidase
2. Transferases
  2.7 Transferring phosphorous-containing groups
      2.7.1    Phosphotransferases with CH—OH as acceptor
            1. hexokinase
            2. glucokinase
            15. ribokinase
            28. triokinase
            40. pyruvate kinase
      2.7.5    1. phosphoglucomutase
3. Hydrolases
  3.1 Acting on ester bonds
      3.1.1    Carboxylic ester hydrolases.
            7. cholinesterase
            8. pseudo cholinesterase
      3.1.3    Phosphoric monoester hydrolases
            1. alkaline phosphatase
            2. acid phosphatase
            9. glucose-6-phosphatase
            11. fructose diphosphatase
      3.1.4    Phosphoric diester hydrolases
            1. phosphodiesterase
            3. phospholipase C
  3.2 Acting on glycosyl compounds
      3.2.1    Glycoside hydrolases
            1. alpha amylase
            2. beta amylase
            4. cellulase
            17. muramidase
            18. neuraminidase
            21. beta glucosidase
            23. beta galactosidase
            31. beta glucuronidase
            35. hyaluronidase
      3.2.2    Hydrolyzing N-glycosyl compounds
            5. DPNase
4. Lyases
  4.1 Carbon-carbon lyases
      4.1.2    Aldehyde lyases
            13. aldolase
      4.2.1    Hydro-lyases
            1. carbonic anhydrase
5. Isomerase
  5.4 Intramolecular transferases
      5.4.2    Transferring phosphoryl group
            triose phosphate isomerase These enzymes listed above may be used individually or in combination or in conjunction with other enzymes, where the other enzymes are part of the signal producing system and may be involved as conjugates or may be unconjugated where they interact with a product of the conjugated enzyme or provide a product which interacts with a product of the conjugated enzyme or interact with a signal label that is a substrate.

Of particular interest in the subject invention is the use of coupled catalysts, usually two or more enzymes, where the product of one enzyme serves as the substrate of the other enzyme or the two enzymes each produce a product which interacts in the signal producing system. Where the first enzyme is bound to a particle, and the signal label conjugate has second enzyme, the particle provides an environment which will enhance the localized concentration of the product of the first enzyme in the environment of the second enzyme, as compared to the bulk solution. Therefore, the turnover by the second enzyme of the first enzyme's product will be greater at the solid surface of the particle than in the bulk solution. This will result in an enhancement of the observed signal when the signal label conjugate is bound through specific binding pair interaction to the surface of the particle.

Various combinations of enzymes may be employed. In one set of combinations, the ability to measure NAD and NADP or their reduced products is employed. In these combinations, oxidoreductases dependent on NAD are employed with an enzyme which provides a substrate for the oxidoreductases. A wide variety of enzyme types and reactions may be employed to produce the substrate, many of the enzymes being part of carbohydrate metabolism. A substantial number of these enzymes will be involved in the formation and transformation of phosphate esters. Among other reactions which may be involved are carbon-carbon bond cleavage by lyases, isomerization involving keto-aldehyde transformations, and decarboxylation.

Of particular interest are combinations involving sugars, where in a first step a transferase, hydrolase, lyase or isomerase, particularly involving a phosphate ester, produces a substrate of a NAD(P) dependent oxidoreductase. Particularly useful are mono-phosphate mono-sacharides of from 3 to 6 carbon atoms as enzyme substrates in the oxidoreductase reaction.

The following table indicates a number of illustrative examples where precursors for oxidoreductases are formed and the course of the reaction of the NAD dependent enzymes is followed by the transformation of the NAD or NADP to or from its reduced form. In each example both enzymes are signal labels.

TABLE IV

| | Category I.U.B. | Enzyme | Exemplary Reaction |
|---|---|---|---|
| 1. | 2.7.1 | Hexokinase | glucose + ATP → glucose-6-phosphate + ADP |
| | 1.1.1 | glucose-6-phosphate dehydrogenase | glucose-6-phosphate + NADP → 6-P-glucuronate + NADPH |
| 2. | 4.1.2 | aldolase | fructose-1,6-diP → dihydroxyacetone-P + glyceraldehyde-3-P |
| | 1.2.1 | glyceraldehyde-P dehydrogenase | glyceraldehyde-3-P + NAD → 3-phosphoglycerate + NADH |
| 3. | 3.1.3 | alkaline phosphatase | dihydroxyacetone diphosphate → dihydroxyacetone phosphate |
| | 1.2.1 | glycerol-3-P dehydrogenase | dihydroxyacetone phosphate + NADH → glyceryl phosphate + NAD |
| 4. | 2.7.1 | pyruvate kinase | phosphoenol pyruvate + ADP → pyruvate + ATP |
| | 1.1.1 | lactate dehydrogenase | pyruvate + NADH → lactate + NAD |
| 5. | 3.1.3 | alkaline phosphatase | 1,6-glucosyl diphosphate → G-6-P |
| | 1.1.1 | glucose-6-phosphate dehydrogenase | G-6-P + NADP → 6-P-glucuronate + NADPH |
| 6. | 5.4.2 | triose phosphate isomerase | glyceraldehyde-3-P → dihydroxyacetone phosphate |
| | 1.2.1 | α-glycerol-3-P | dihydroxyacetone phosphate + NADH → glyceryl phosphate + NAD |

TABLE IV-continued

| Category I.U.B. | | Enzyme | Exemplary Reaction |
|---|---|---|---|
| | | dehydrogenase | |
| 7. | 3.1.3 | alkaline phosphatase | D-sorbitol phosphate → D-sorbital |
| | 1.1.1 | α-D-hexitol dehydrogenase | D-sorbital + NADP → α-D-glucopyranose + NADPH |
| 8. | 5.4.2 | phosphoglucomutase | α-glucose-1-phosphate → glucose-6-phosphate |
| | 1.1.1 | glucose-6-phosphate dehydrogenase | glucose-6-phosphate + NAD → 6-P-glucuronate + NADH |
| 9. | 4.1.1 | pyruvate decarboxylase | pyruvate → acetaldehyde |
| | 1.1.1 | alcohol dehydrogenase | acetaldehyde + NADH → ethanol + NAD |
| 10. | 4.2.1 | fumarase | fumarate → malate |
| | 1.1.1 | malate dehydrogenase | malate + NAD → oxalacetate + NADH |
| 11. | 4.2.1 | aconitase | cis-aconitate → isocitrate |
| | 1.1.1 | isocitrate dehydrogenase | isocitrate + NAD → α-oxoglutarate + NADH |

Another combination of enzymes involves the formation of hydrogen peroxide, where the resulting catalyzed reaction by peroxidase of the hydrogen peroxide with a chemiluminescent material, e.g. luminol, produces light. Besides luminol, other 2,3-dihydro-1,4-phthalazinediones may be employed. These include the 5-amino-6,7,8-trimethoxy- and dimethylamino[cal]benz analog. Other compounds are the 2,4,5-triphenylimidazoles, with lophine, as the common name for the parent, and the para-dimethylamino and -methoxy substituted compounds also finding use. The chemiluminescent compound may be the direct source of light or may be allowed to interact with an acceptor, such as 9,10-dibromoanthracene, which will then emit light. Alternatively one can provide a wide variety of dye precursors which will undergo enzymatically catalyzed reactions with hydrogen peroxide to produce the colored form which can be detected.

The following table indicates a number of these reactions in which both enzymes are signal labels.

TABLE V

| Enzyme Category | | Enzyme | Exemplary Reaction |
|---|---|---|---|
| 1. | 1.1.3 | glucose oxidase | glucose + $O_2$ → glucuronate + $H_2O_2$ |
| | 1.11.1 | peroxidase | $H_2O_2$ + luminol → products + hν |
| 2. | 1.7.3 | uricase | urate + $O_2$ → allantoin + $H_2O_2$ |
| | 1.11.1 | peroxidase | $H_2O_2$ + O-dianisidine → dye |
| 3. | 1.4.3 | D-amino acid oxidase | D-alanine + $O_2$ → pyruvate + $H_2O_2$ |
| | 1.11.1 | catalase | $H_2O_2$ + $Fe(CN)_6^{-4}$ → $Fe(CN)_6^{-3}$ |
| 4. | 1.2.3 | xanthine oxidase | xanthine + $O_2$ → uric acid + $H_2O_2$ |
| | 1.11.1 | cytochrome C oxidase | $H_2O_2$ + pyrogallol → hydroxyquinone |

The next series of reactions are those which are based on two reactions involving water, normally the two reactions involving hydrolases, although synthetases may also be employed.

TABLE VI

| Enzyme Category | | Enzyme | Exemplary Reaction |
|---|---|---|---|
| 1. | 3.1.3 | alkaline phosphatase | 1-umbelliferyl-β-galactoside-6-P → umbelliferyl-β-galactoside |
| | 3.2.1 | β-galactosidase | 1-umbelliferyl-β-galactoside → umbelliferone |
| 2. | 3.1.1 | acetylesterase | 1-alizarinyl-β-glucoside-monoacetate → 1-alizarinyl-β-glucoside |
| | 3.2.1 | β-glucosidase | 1-alizarinyl-β-glucoside → alizarin + glucose |
| 3. | 3.2.1 | glucoamylase | 1-(p-nitrophenyl) 4-0-α-D-glucopyronosyl β-D-glucose → 1-(p-nitrophenyl) β-D-glucoside |
| | 3.2.1 | β-glucosidase | 1-(p-nitrophenyl) β-D-glucoside → p-nitrophenoxide + |
| 4. | 3.1.1 | cholinesterase | phenolphthalein β-glucuronide choline chloride ester → phenolphthalein β-glucuronide |
| | 3.2.1 | β-glucuronidase | phenolphthalein β-glucuronide → β-glucuronide + phenolphthalein |
| 5. | 3.4.1 | proline iminopeptidase | L-prolyl-L-leucine p-nitroanilide → L-leucine p-nitroanilide |
| | 3.4.1 | aminopeptidase | L-leucine p-nitroanilide → L-leucine + p-nitroaniline |
| 6. | 3.5.1 | urease | urea + $H_2O$ → $CO_2$ + $NH_3$ |
| | 6.3.5 | NAD synthetase | ATP + deamidoNAD + $NH_3$ + $H_2O$ → ADP + NAD + pyrophosphate |
| 7. | 3.1.3 | alkaline phosphatase | 2,6-dichlorophenolindophenol-P → 2,6-dichlorophenolindophenol |
| | | peroxidase | 2,6-dichlorophenolindophenol + $H_2O_2$ → dye |

The next series of combinations involves the preparation of a substrate in a first step for an enzyme which can donate or receive electrons from an acceptor or donor, with the result that there is a substantial change in the absorption spectrum of the acceptor or donor. For the most part, the second enzyme will be an oxidoreductase, particularly dehydrogenases and oxidases. In this series, both enzymes are signal labels.

TABLE VII

| Enzyme Category | Enzyme | Exemplary Reaction |
|---|---|---|
| 1. 3.1.1 | cholinesterase | butryl choline chloride → choline |
| 1.1.99 | choline dehydrogenase | choline + phenazine methosulfate → betaine aldehyde + dye (H) |
| 2. 2.7.1 | glycerol kinase | ATP + glycerol → L-glycerol-3-P |
| 1.1.99 | glycerolphosphate dehydrogenase | L-glycerol-3-P + methylene blue → dihydroxyacetone phosphate + dye (H) |
| 3. 1.1.1 | glucose dehydrogenase | $\beta$-D-glucose + NADP → D-glucono-$\delta$-lactone + NADPH |
| 1.1.99 | glucinate dehydrogenase | D-gluconate + resazurin → 2-keto-D-gluconate + dye (H) |
| 4. 1.1.1 | alcohol dehydrogenase | ethanol + NAD → acetaldehyde + NADH |
| 1.6.2 | cytochrome $b_5$ reductase | NADH + indigo tetrasulfonate → NAD + indigotetra sulfonate (H) |
| 5. 4.1.2 | deoxyriboaldolase | 2-deoxy-D-ribose-5-phosphate → D-glyceraldehyde-3-P + acetaldehyde |
| 1.2.3 | aldehyde oxidase | acetaldehyde + 2,6-dichlorophenol-indophenol → acetic acid + dye (H) |
| 6. 1.1.1 | alcohol dehydrogenase | ethanol + NADP → acetaldehyde + NADPH |
| 1.6.99 | reduced NADP dehydrogenase | NADPH + trichlorophenolindophenol → NADP + trichlorophenolindophenol (reduced) |

In the subject invention, therefore, combinations are employed where a first enzymatic reaction is involved to provide a substrate for a second enzymatic reaction. The second enzymatic reaction involves the production of a compound which can be determined spectrophotometrically due to absorption of light, particularly over 300 nm, preferably over 350 nm, and more preferably over 400 nm, fluorescence, where the light emitted is of a wavelength greater than 350 nm, preferably greater than 400 nm, and more preferably greater than 450 nm or through chemiluminescence. The extinction coefficient should be greater than $10^3 lmol^{-1}cm^{-1}$, preferably greater than $10^4$ for absorption above the indicated wavelengths.

As an alternative to having a first enzyme whose product is the substrate of a second enzyme, one can employ an enzyme which produces a product which interacts with a second compound. The second compound may be initially provided in the medium as a label, may be produced through an enzymatic reaction, or may react through the intermediacy of a non-enzymatic catalyst. The two phenomena involved will normally be either (1) energy transfer from an excited molecule to another molecule which thereby becomes excited, the second molecule then emitting light, or (2) production of a compound which can react through the intermediacy of a non-enzymatic catalyst to produce a compound which will normally absorb light at relatively long wavelengths. The following table is illustrative of a number of these combinations where the signal labels are the enzyme and the underlined compound.

TABLE VIII

| Enzyme Category | Catalyst | Exemplary Reaction |
|---|---|---|
| 1. 3.2.1 | $\beta$-galactosidase | di($\beta$-galactosidyl) fluorescein → mono-($\beta$-galactosidyl) fluorescien |
| | | umbelliferone + h$\nu$ → umbelliferone* |
| | | umbelliferone* + mono-($\beta$-galactosidyl) fluorescein → umbelliferone + mono-($\beta$-galactosidyl)-fluorescein* mono-($\beta$-galactosidyl) fluorescein* → mono-($\beta$-galactosidyl) fluorescein + h$\nu^1$ |
| 2. 3.1.3 | alkaline phosphatase | fluorescein diphosphate → fluorescein mono-phosphate |
| 1.11.1 | peroxidase | luminol + $H_2O_2$ → aminophthalate* |
| | | aminophthalate* + fluorescein mono-phosphate → aminophthalate + fluorescein mono-phosphate* |
| | | fluorescein mono-phosphate* → fluorescein mono-phosphate + h$\nu$ |
| 3. 1.1.1 | glycerol-3-P dehydrogenase (Meldola Blue) | glycerol-3-P + NAD → dihydroxyacetone-P + NADH |
| | | NADH + iodonitro triphenyltetrazolium (INT) → NADH + iodonitro-triphenylformazan |
| 4. 1.1.1 | lactate dehydrogenase (phenazinemethosulfate) | lactate + NAD → pyruvate + NADH |
| | | NADH + methyl viologen → NAD + Dye (H) |
| 5. 1.1.1 | 3-hydroxybutyrate dehydrogenase (pyocyanine) | 3-hydroxybutyrate + NAD → acetoacetate + NADH |
| | | NADH + INT → NAD + iodonitrotriphenylformazan |
| 6. 1.11.1 | microperoxidase | luminol + $H_2O_2$ → aminophthalate* |
| | | aminophthalate* + fluorescein → fluorescein* + aminophthalate |
| | | fluorescein* → fluorescein + h$\nu$ |

While the above exemplary combinations have been limited to two components as labels, it is obvious, that three or more components may be used. There are advantages and disadvantages in the proliferation of the number of labels in the signal producing system. By having three labels, for example, three enzymes, one can have the second and third enzymes, so far as the succession of the product of one being the substrate of the next, as part of the particle conjugate and the first enzyme as the label bound to the specific binding pair member. In this way, less signal will initially be produced as a result of the first enzyme in the bulk solution. However, it should be appreciated, that the concentrations at the surfaces of the particles of the products from the enzymes in the successive series of reactions will be progressively smaller the greater the number of reactions which must occur. Thus, the slower the overall reaction and the greater the number of reactions which must occur, the longer the period of time which will be required to obtain a measurable signal. Therefore, one must compromise to some degree between minimizing the background value and minimizing the time to a measurable signal.

In the signal producing system either one or a plurality of enzymes may be employed and the properties of the particle can be employed in a variety of ways to affect the enzyme reactions.

With a single enzyme, the particle can provide an environment which has a significant effect on the enzyme turnover rate, due to the nature of the particle. This can be as a result of a different pH, ionic strength, hydrophobic environment, etc. in the ambit of the particle as compared to the bulk solution. Therefore, one can add salts, buffers, ionic polymers, ancillary solvents, or the like, and by appropriate choice of the particle, create a substantial gradient in properties between the bulk solution and the particle environment.

Alternatively, one can employ the particles to provide a different rate of diffusion. The signal producing system will then employ an enzyme labeled binding pair member conjugate and a macromolecular enzyme substrate or inhibitor e.g. antienzyme, pseudosubstrate, or irreversible inhibitor. Particularly useful enzyme inhibitors are active site directed irreversible inhibitors. Exemplary of such inhibitors are fluorophosphonates which react with cholinesterase and aryl mercuric salts which react with sulfhydryl groups of hydrolases. Alternatively, uncompetitive inhibitors may be employed such as sulfonamides for carbonic anhydrase. The appropriate inhibitor would be covalently conjugated to a large macromolecule at a position which would not interfere with the inhibitory effectiveness of the inhibitor. The enzyme labeled binding pair member conjugate which becomes bound to the particle will not react to any substantial degree with the macromolecular species, while the enzyme in the bulk solution will.

The effect of association of the enzyme with the particle should provide at least a two, preferably a 10 fold, and more preferably a 100 fold rate difference than if the enzyme were in the bulk solution.

The above techniques can also be employed where more than one enzyme is involved in the particle environment. For example, where two sequential enzymes are involved, an enzyme receptor e.g. antienzyme, can be employed which when bound to enzyme substantially reduces the enzyme turnover rate. Enzyme in the bulk solution will be inhibited while enzyme in the particle environment will be protected. The effect will be to substantially eliminate background signal.

In addition, reagents can be added to the assay medium that are sterically excluded from the particle conjugate and act as scavengers to reduce the signal generated in the bulk solution. These can include reagents that scavenge product from the first enzyme in the bulk solution, either being generated by first enzyme in the bulk solution or escaping from the particle to which the first enzyme is bound. These reagents include enzymes different from the first and second enzymes, receptors for the product of the first enzyme or chemical reactants that react with such product.

A wide variety of non-enzymatic catalysts are described in U.S. Patent Application Ser. No. 815,636, the appropriate portions of which are incorporated herein by reference. The non-enzymatic catalyst employs as its reactants a first compound which reacts by a one-electron transfer and a second compound which reacts by a two-electron transfer, where the two reactants are capable of reacting with each other slowly, if at all, in the absence of the catalyst.

Besides enzymes as labels, one can also have chromogenic materials as labels, particularly compounds which fluoresce or chemiluminesce. By bonding the chromogenic label to a member of the specific binding pair, and having the homologous member bound to the solid phase, the two members will associate, with the chromogenic label being introduced onto the solid phase. Where the environment of the solid phase affects the fluorescence, the observed signal will be related to the partition of the fluorescer between the solid and liquid phase. Alternatively, by adding as the macromolecular reagent, receptor for the chromogenic member (antichromogen), which may or may not be conjugated to a quencher, or a macromolecular reagent that reacts with the chromogenic member, the rate of diffusion for the added reagent into the particle will be substantially slower than the rate of diffusion in the bulk solution. Illustrative reagents are chemicals such as peracids, e.g. percarboxylic acids, opaque absorbents e.g. charcoal, and the like. Where the reaction of the macromolecular reagents with the chromogen results in quenching of the chromogen, the more of the chromogen on the solid phase, the slower the rate at which the observed signal will diminish. A technique similar to this, employing antibodies to inhibit the binding of the antichromogen to the chromogen may be found in U.S. Pat. No. 3,998,943.

Besides molecules which are fluorescent, chemiluminescent molecules may also be used, which will transfer energy to an acceptor which will then fluoresce. Since the chemiluminescent reaction can be limited to the solid phase by binding an enzyme as a signal label conjugate to the particle, which enzyme provides for the chemiluminescent reaction, and having an acceptor as a label bound to the specific binding pair member, one can monitor the increased localized concentration of the chemiluminescent species on the solid phase produced by association of the signal label conjugate with the particle.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-0, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)bis-benzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonapht-hyl hydrazone of hellebrigenin, chlortetracycline, N-(7-dimethylamino-4-methyl-2-oxo--chromenyl) maleimide, N-[p-(2-benzimidazoyl)-phenyl] maleimide, N-(4-fluoranthyl) maleimide, bis(homovanillic acid), resazarin, 4-chloro-7-nitro-2.1.3.-benzooxadiozole, merocyanine 540, resorufin, rose bengal, and 2,4-diphenyl-3(2H)-furanone.

It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

However, while the aforementioned labels will be more commonly employed, other types of labels may also find use, such as stable free radicals, including their creation and destruction, labels for pontentiometric determination, and the like.

Particles

A wide variety of particles may be employed in this invention. The particles are preferably porous or microreticulated, that is, have areas open to the bulk solution, which are greater than about 50% encompassed by the particle material. These areas can be deep pores, channels, fractures, indentations or the like.

The particles which are employed are chosen to create an environment for one or more members of the signal producing system which allows for differentiation between the signal label bound to the particle surface and the signal label in bulk solution. By appropriate employment of macromolecular reagents, one can limit the accessibility of a signal label on the particle surface to the macromolecular reagent. The pores or channels of the particle are chosen to permit access of at least one member of the signal producing system and frequently to inhibit access of at least one, usually one, member of the signal producing system.

The porous particles can come with various pore sizes. The pore size will be chosen in accordance with the property of the particle which is being employed. Where the diffusion rate is a significant factor, one will employ a cut-off size between the molecules which must diffuse into the pores and the molecules which are inhibited from diffusing into the pores. Cut-off sizes can vary from tens of thousands e.g. 20,000, more usually 40,000 to millions molecular weight e.g. 20,000,000, more usually 10,000,000 and various ranges are commercially available.

The size of the particle is limited by the following considerations. The particles should be relatively stably dispersed during the time of the assay and preferably longer. Indefinite stability in the assay medium is not required. The particle size should be sufficiently small, so that a large number of particles will be in the solution. That is, one does not wish to see wide fluctuations in the signal, where one or a few particles passing through the light path make a substantial change in the observed signal. Therefore, for the most part, the particles will be of a diameter in the range of about 50 nm to $100\mu$, more usually about 500 nm to $25\mu$. Pores sizes will generally vary from about 0.1 nm to under 750 nm, more usually not more than about 500 nm.

The particle size can be varied and surface area increased by breaking larger particles into smaller particles by mechanical means, such as grinding, sonication, agitation, etc.

A wide variety of materials may be employed for the particles. Many materials are commercially available or commercially available materials may be modified, so as to modify the properties of the material.

The particles can be derived from naturally occurring materials, naturally occurring materials which are synthetically modified and synthetic materials. Of particular interest are polysaccharides, particular crosslinked polysaccharides, such as agarose, which is available as Sepharose, dextran, available as Sephadex and Sephacyl, cellulose, starch and the like. Other materials include polyacrylamides, polystyrene, polyvinyl alcohol, copolymers of hydroxyethylmethacrylate and methyl methacrylate, silicones, glasses, available as Bioglas, charcoal and the like.

The particles should be polyfunctional or be capable of being polyfunctionalized. A wide variety of functional groups are available or can be incorporated. Functional groups include carboxylic acids, aldehydes, amino groups, cyano groups, ethylenic groups, hydroxyl groups, mercapto groups, and the like. The manner of linking a wide variety of compounds to the various particles is well known and is amply illustrated in the literature. See for example, Cuatrecases, J. Biol. Chem. 245, 3059 (1970).

The length of the linking groups will vary widely depending upon the nature of the compound being linked, the effect of distance between the label and the particle on the labels properties, the potential for crosslinking of the label, and the like.

The particle, whether swelled or unswelled by the aqueous medium, will define a volume in the aqueous medium where the environment of the fluid in the particle environment is different from the environment of the fluid in the bulk solution. That is, the fluid in the pores and/or channels and/or on the surface of the particle will be subjected to the particles chemical and physical influence.

If one wishes to provide a pH gradient, then the particle can be substituted with positively or negatively charged groups, such as ammonium, sulfonate, carboxylate and the like, or by attaching an enzyme to the particle which has a product of different acidity from its substrate. By employing a buffer having a relatively weak buffering capacity, a pH gradient can be achieved between the particle and the bulk solution.

Depending upon the nature of the particle, the rate of diffusion can be impeded as compared to the bulk solution. The size of the channels, the nature of the channels, straight or curved, and the chemical nature of the particles can all serve to affect the rate of diffusion of a molecule in a channel or pore.

Particle Conjugate

The particle conjugate will always be conjugated to one of the members of the specific binding pair. The conjugation may be direct or indirect. By direct conjugation is intended covalent bonding of the specific binding pair member label to the particle. Alternatively, one can employ receptor for the specific binding pair member. Where the specific binding pair member is multivalent an impure preparation of a complementary member may be covalently bonded to the particle. Noncovalent binding of the unpurified specific pair member then gives a particle labelled with the signal labelled or unlabelled homologous pair member free of contaminants. The resulting particle conjugate may then be used in the assay with its complementary signal label conjugate.

A modification of the above situation may be employed where the analyte is a receptor such as human IgE. One could covalently bond an allergen recognized by the IgE to the particle. As a member of the signal label conjugate one could use sheep anti(human IgE). In the assay, the human IgE analyte would bind to the allergen on the particle and the signal label conjugate (anti(human IgE)) would bind to the human IgE bound to the particle. This situation differs from the general situation since the binding of the analyte to the particle during the assay produces what has been defined as the particle conjugate. Also, other receptors such as IgA, IgG, IgM, enzymes, specific receptors such as for estriol, biotin or other drugs, etc. may be similarly employed.

In effect, there are two specific binding pairs, where the same compound plays the role of antigen in one pair and receptor in the other, while the complementary members to the analyte of each of the specific binding pairs need not have any relationship of ligand and receptor.

The ratio of the specific binding pair member to the molecular weight of the particle will vary widely, depending upon the nature of the particle, the available surface area, the available binding sites, and the like. There will be on the average at least about one specific binding pair member per particle and generally at least about one per $1 \times 10^5$ molecular weight, more usually at least about one per $1 \times 10^7$ molecular weight.

For many of the signal producing systems, one or more signal labels other than in the signal label conjugate will be employed, usually covalently bonded to the particle. As indicated previously, these labels may be enzymes, catalysts, chromogens electron transfer agents, phosphors or the like. The ratio of the signal label to the particle molecular weight will vary widely, depending upon the nature of the label, as well as the nature of the signal producing system. Where there is a signal label, there will be on the average at least about one signal label per particle and generally at least about one per $1 \times 10^3$ molecular weight, more usually at least about one per $1 \times 10^6$ molecular weight.

Novel compositions can be prepared as particle conjugates. Particularly any of the haptenic or antigenic ligands listed in the analyte section or any of the receptors can be conjugated to the particle in conjunction with a member of the signal producing system.

Of particular interest are conjugates with the particles of poly(amino acids), such as albumins, globulins, particularly immunoglobulins, hormones, antigens diagnostic of disease e.g. CEA, lipoproteins, glycoproteins, and the like, as well as polysaccharides, such as aminoglycosides, lipopolysaccharides, neuraminic acids, and the like, in conjunction with labels, such as enzymes and chromogen e.g. fluorescers and quenchers.

Illustrative of particle conjugates which find use in the invention are polysaccharide particles, such as agarose, dextran and cellulose conjugated with at least one poly(amino acid) antigen molecule and at least one member of the signal producing system, such as an enzyme, chromogen, chemiluminescer, electron transfer agent or phosphor. The preferred enzymes have been described previously. As indicated, the enzymes would have a product which is the substrate of the next enzyme or vice versa. Particularly, hydrolases will find use, such as phosphatases, glycosidases, and esterases, transferases, such as kinases, and oxidoreductases, such as dehydrogenases and peroxidases. As the chromogens, fluorescers, quenchers, and chemiluminescers would find particular application. As catalysts, Meldola blue would find particular application, while as phosphors, polycyclic aromatics and rare earth chelates, are of particular interest.

Binding pair member conjugate

The conjugation of labels to ligands and receptors, has been amply reported in the literature, particularly in the references cited previously. Mole ratios of labels to specific binding pair member will vary widely, depending upon the nature of the label as well as the nature of the specific binding pair member.

Illustrative conjugates include enzyme-ligand or -receptor conjugates, substrate- or cofactor-ligand or -receptor conjugates, chromogen-ligand or -receptor, catalyst-ligand or -receptor conjugates, where one or more of the labels may be present in the conjugate. The ligands, and labels have been previously described. Also, the manner of conjugation is conventional and has been amply described or is described in the prior art.

Ancillary Materials

Various ancillary materials may be employed in the subject assays. Particularly, enzyme substrates, cofactors, and inhibitors may be conjugated to hub nuclei in a manner where they retain their effectiveness, but are inhibited from entering the pores of the particle. Where an enzyme substrate is bonded to a hub nucleus, the enzyme reaction will for the most part take place in the bulk solution, so that enzyme in the particle will be relatively inactive. In this manner, where an enzyme-specific binding pair member conjugate is employed, the more of the conjugate which is bound in the particle, the smaller the detected signal.

By contrast, where enzyme inhibitors are employed, the enzyme in the bulk solution will be substantially inhibited, with the enzyme in the particle protected from the inhibitor.

Various hub nuclei can be used, both nuclei which have been described for the particles, as well as other nuclei, such as polypeptides, proteins, nucleic acids, other synthetic polymers, and the like. A list of potential inhibitors may be found in co-pending Application Ser. No. 815,487, filed Aug. 14, 1977, now U.S. Pat. No. 4,233,401.

Kits

As a matter of convenience, the reagents can be provided as kits, where the reagents are in predetermined ratios, so as to substantially optimize the sensitivity of the assay in the range of interest. After reconstitution of the reagents, the particle conjugate will normally be dispersed in an aqueous medium of substantially the same density as the particle, so that the particles remain substantially uniformly dispersed or dispersable. By employing high density additives or adjusting the density of the particles, the desired density can be achieved.

Of particular interest as additional reagents in the signal producing system: when enzymes are employed, scavenger macromolecular reagents bearing enzymes, enzyme inhibitors or substrates, and antienzymes; when chromogens are employed, antifluorescer, optionally bearing quencher, antichemiluminescer, scavenger macromolecular reagents bearing quencher and chromogen reactants which create or destroy the chromophoric functionality.

The signal label conjugate may be in the same or different container from the particle conjugate, depending on whether the specific binding pair members are the same or different respectively. Both conjugates may be lyophilized or in an aqueous medium concentrate having stabilizers, such as bacteriostats, bacteriocides, and proteins. Included with either or both of the reagents may be buffers, members of the signal producing system such as enzyme substrates and cofactors, or the like.

In some instances, it may be desirable to provide as a single reagent, with the specific binding pair members non-covalently bound to each other, the particle conjugate and the signal label conjugate. The combination may be preprepared or prepared in situ.

EXPERIMENTAL

The following examples are offered by way of illustration and not by way of limitation.

(All percents and parts not otherwise indicated are by weight, except for mixtures of liquids which are by volume. All temperatures not otherwise indicated are centigrade. The following abbreviations are employed: G6PDH-glucose-6-phosphate dehydrogenase; HK-hexokinase; HIgG human γ-globulin; EDTA-ethylene diaminotetraacetic acid; NHS-N-hydroxysuccinimide; NADH-nicotinamide adenine dinucleotide reduced; Ranti HIgG-rabbit anti(human IgG); ONPG-o-nitrophenyl galactoside; r.t.-room temperature; RIgG-rabbit IgG; RSA-rabbit serum albumin; OAc-acetate; AP-alkaline phosphatase; PBS-phosphate buffered saline, β-Me-β-mercaptoethanol; EDCI-ethyl diamethylaminopropyl carbodiimide.

EXAMPLE 1

Preparation of Sepharose4B Conjugate with G6PDH and HIgG

Into a reaction flask was introduced 2.5 mg G6PDH, 16 mg glucose-6-phosphate, 90 mg NADH, 0.19 mg HIgG, and 0.25 g of moist cyanogen bromide activated Sepharose4B (obtained from Pharmacia and washed in 1 mM HCl, 200 ml) in 0.1 M sodium bicarbonate, pH 8.1, 0.5 M NaCl and the mixture stirred at 40° for six hours, followed by stirring for two hours at room temperature. To the solution was then added 0.25 ml of 1 M 2-aminopropanol, pH 8.0 and the reaction allowed to stir overnight at 4°. The reaction mixture was then washed by centrifugation 3×2 ml 0.1 M borate, pH 8.5, 1 M NaCl, followed by 2×2 ml of 0.1 M sodium bicarbonate 0.5 M NaCl, pH 8.1, 0.05% azide. After assaying for enzyme activity, the samples were washed again and suspended in 0.1 M sodium bicarbonate, 2 mg/ml bovine serum albumin, 0.05% azide. Employing a 2.5 μl aliquot of a total volume of 1.4 ml having approximately 0.5 ml packed beads, the enzyme activity was found to be 12.1 U/ml.

The amount of HIgG was found to be 129 μg/ml or 10.6 μg/per U of enzyme.

EXAMPLE 2

Conjugation of rabbit antiHIgG with HK

Into a reaction flask was introduced 10.2 mg of rabbit antiHIgG in 1.2 ml of 0.1 M phosphate, pH 7.5, 10 mM EDTA, 0.2 ml dimethylformamide and 50 μl of a 10 mg/ml solution (added in 25 μl aliquots) of meta-maleimidobenzoic acid NHS ester and the mixture stirred for 30 min at room temperature. The reaction mixture was then chromatographed on a 2.5×25 cm G50 column equilibrated with $N_2$ purged 0.1 M phosphate, pH 6, 10 mM EDTA and 2 ml fractions collected. Fractions 14 to 16 were pooled. To 3.7 ml of 0.1 M phosphate, pH 7.5, 10 mM EDTA containing 13.5 mg HK, was added 50 μl 2 M glucose and 0.4 ml DMF and the mixture stirred under nitrogen at room temperature. To the solution was added 100 μl in four aliquots of a 20 mg/ml solution of S-acetylmercaptosuccinic anhydride in DMF over a period of about one hour. After completion of the addition and an additional ten minute period for reaction to occur, 0.4 ml of 1 M hydroxylamine, pH 7.5, was added with stirring under nitrogen and the mixture stirred for 60 min at room temperature.

The reaction mixture was then chromatographed on a 2.5×25 cm G50 column in 0.1 M phosphate, pH 6, 10 mM EDTA, nitrogen purged, and eluted in 2 ml fractions, with fractions 16 to 19 pooled. The total volume of the pooled fractions was 7.5, which contained 8.96 mg of protein. Analysis: 5.7 SH groups per hexokinase. Since the hexokinase contains 4 SH groups, approximately two additional SH groups were added per hexokinase. To 7.3 ml of the hexokinase solution prepared above was added 3.5 ml of the derivatized rabbit antiHIgG (5.25 mg), the aqueous medium being 0.1 M phosphate, pH 6, 10 mM EDTA, 30 mM glucose, and nitrogen purged. The mixture was allowed to react at 4° for 48 hrs.

The reaction mixture was then chromatographed on a BiogelA5M column in 0.1 M phosphate, pH 7, 10 mM EDTA, 2 mM β-Me 0.02% azide, the column nitrogen purged, and the mixture applied to the column in 6 ml and eluted in 3.5 ml fractions. Fractions 45 to 68 were pooled and concentrated to approximately 8 ml. The resulting conjugate was found to have about 0.36U/μg; 2.9 mg of HK and 2.50 mg of antiHIgG were coupled.

EXAMPLE 3

Labelling of RIgG (Rabbit γ-globulin) with $C^{14}$ Succinic anhydride

RIgG solution (2 ml) was dialyzed against 350 ml of 0.1 M sodium phosphate buffer, pH 7.6, over 48 hrs with one change. The dialyzed solution had a concentration of 13.0 mg/ml RIgG (by u.v.).$C^{14}$-succinic anhydride (50 μ$C_i$, 0.7 mg) was diluted 1:10 with "cold" succinic anhydride and dissolved in acetone to give 0.1 M solution (2.10$^6$ cpm/μmole). This solution (30 μl) was added, at r.t. with stirring to 0.88 ml (11.4 mg) of the dialyzed RIgG solution. After 40 min. of stirring, 155 μl of 2 M hydroxylamine HCl pH 8.0 were added. After stirring for an additional 2 hrs, the reaction mixture was dialyzed at 4° against 350 ml of 0.05 M sodium phosphate buffer pH 7.0 over 72 hrs with six changes. The dialyzed solution (1.07 ml) had a concentration of 11.0 mg/ml RIgG and 1.37×10$^6$ cpm/ml (10 succinic anhydride per RIgG).

EXAMPLE 4

Functionalizing RIgG with sulfhydryl groups

S-Acetylmercaptosuccinic anhydride (1.85 mg) in 25 μl of dry DMF was added slowly at r.t. to a stirred solution of 5.5 mg RIgG (previous example) in 1.0 ml of 0.05 M sodium phosphate, pH 7.5, with 0.02 M EDTA, under a nitrogen atmosphere. After 10 min. of stirring, 0.1 ml of 1.0 M hydroxylamine HCl pH 7.5 was added and the stirring was continued for an additional 10 min. The reaction mixture was chromatographed on 0.9×10.5 cm G-25 fine Sephadex column (degassed and saturated with argon) with 0.05 M sodium phosphate buffer, pH 5.0, with 0.02 M EDTA (degassed and saturated with argon). Fractions (0.8 ml) were collected at a rate of 0.125 ml/min. Fractions 5-7 were pooled to give 2.5 ml containing 4.3 mg RIgG (on basis of radioactive counting).

EXAMPLE 5

Functionalizing alkaline phosphatase with maleimido groups

Alkaline phosphatase (1 ml, 5.0 mg, 5075 I.U.) suspension was spun down, the supernatant removed, the precipitated enzyme dissolved in 1.0 ml of 0.05 M sodium phosphate buffer, pH 7.0 and dialyzed against 500 ml of the same buffer in the cold over 48 hr with four changes. The dialyzed solution was stirred and 0.4 mg m-(N-maleimido)benzoic acid N-hydroxysuccinimide ester in 40 μl of dry DMF was added. After 30 min of stirring, the reaction was terminated by addition of 0.4 ml of 1 M sodium acetate buffer pH 5.0. The reaction mixture was chromatographed on 0.9×25 cm G-25 fine Sephadex column with 0.02 M sodium acetate buffer, pH 5.0; fractions of 1.0 ml were collected with a flow rate of 0.125 ml/min. Fractions 6-7 were pooled to give 2.15 ml with 2.54 mg alkaline phosphatase (based on u.v.).

EXAMPLE 6

Conjugation of RIgG and alkaline phosphatase

The alkaline phosphatase solution was made 0.02 M in EDTA and the pH was adjusted to 6.5. The solution was stirred under nitrogen and the RIgG-SH solution (Example 4) was added slowly. The pH was brought to 6.7 and the reaction mixture was stirred at r.t. for 3 hrs and overnight at 4°. After addition of 0.2 ml 0.02 M mercaptoethanol solution and stirring at r.t. for 30 min, the reaction mixture was kept over 72 hrs. at 4°. The solution was concentrated to 1 ml volume in Amicon through PM30 Diaflo® ultrafilter and chromatographed on 1.5×87 cm 1.5 M Biogel A column with 0.1 M Tris-HCl pH 7.6 with 0.05 M NaCl and 1 mM MgCl$_2$. Fractions of 1.0 ml volume were collected at a flow rate of 5 ml/hr. Fractions 46-48 (RIgG-AP-I) and 49-60 (RIgG-AP-II) were pooled to give 2.75 ml and 12.1 ml respectively. After determination of the properties of the conjugate, the solutions were stabilized by NaN$_3$, 0.05%, and egg albumin 1 mg/ml.

The following are the properties of the product, as determined by radioactivity counting and UV absorbance.

| Conjugate | Total amt. (mg) | AP/RIgG molar ratio | % enzyme bound | % enzymatic activity |
|---|---|---|---|---|
| RIgG-AP-I | 1.16 | 1.75 | 100% | 4.9% |
| RIgG-AP-II | 3.16 | 0.85 | 100% | 6.0% |

EXAMPLE 7

Conjugation of β-D-Galactosidase and HIgG(human IgG) to Sepharose 4B beads

β-D-Galactosidase (1.0 mg 300 I.U.) as 0.2 ml suspension was spun down, dissolved in 1.0 ml of 0.1 M sodium bicarbonate, 0.5 M NaCl and dialyzed against 1 l. of this buffer at 4° over 24 hrs with one change. Cyanogen bromide activated Sepharose 4B beads (100 mg) were swollen and washed with 10$^{-3}$M HCl solution for 15 min. To the swollen beads was added 1.0 mg of β-D-galactosidase and 1.0 mg of HIgG in 5 ml of 0.1 M sodium bicarbonate buffer with 0.5 M NaCl in a testtube which was rotated end-to-end for 2 hrs at r.t. Unbound material was washed away with coupling buffer and any remaining active groups were reacted with 1 M 2-propanolamine at pH 8.0 for 2 hrs. Three washing cycles were used to remove non-covalently absorbed proteins, each cycle consisting of a wash with 0.1 M sodium acetate buffer containing 0.5 M NaCl followed by a wash with 0.1 M Tris-HCl, pH 8.0, buffer containing 0.05 M NaCl and 1 mM MgCl$_2$. The beads were suspended in 1.5 ml of 0.1 M Tris-HCl, pH 7.0, buffer with 0.1 M NaCl, 1 mM MgCl$_2$ and 0.05% NaN$_3$.

EXAMPLE 8

Preparation of 4-methylumbelliferyl-β-D-(−)-Galactopyranoside-6-phosphate a.

4-methylumbelliferyl-tetra-O-(trimethylsilyl)-β-D-(−)-galactopyranoside (4-MUG-tetra-OTMS)

4-Methylumbelliferyl-β-D-(−)-galactopyranoside (3.0 g), 18 ml hexamethyldisilazane and 12 ml chlorotrimethylsilane were stirred in 80 ml dry pyridine overnight at r.t. under an argon atmosphere. The reaction mixture was evaporated to dryness under reduced pressure, ether was added and the white crystals were removed by filtration. The supernatant was evaporated to give white crystals, which were recrystallized from 30 ml hexane overnight in the cold to afford 4.75 g (80%) of fine white crystals, m.p. 135°–137.5°, tlc, silica, $R_f$ 0.67, ether-hexane 2:1.

b. 4-Methylumbelliferyl-2,3,4-tri-O-(trimethylsilyl)-$\beta$-D-(−)-galactopyranoside (4-MUG-tri-OTMS)

4-MUG-tetra-OTMS (4.7 g) was suspended in 200 ml of cold dry methanol. The cooled (0°) stirred suspension was treated with 50 ml of anhydrous methanol that had been shaken with 220 mg $K_2CO_3$. The suspension dissolved during 45 min of stirring and the resulting solution was carefully neutralized with a dilute solution of glacial acetic acid in dry methanol. The methanol was removed in vacuo at r.t. The residue was taken up in ether, the ether filtered and then evaporated to give 3.2 g of white crystals (tlc, silica, $R_f$ 0.28, ether hexane 2:1)

c. 4-Methyumbelliferyl-$\beta$-D-(−)-galactopyranoside-6-cyanoethyl phosphate

4-MUG-tri-OTMS (3.2 g), 2-cyanoethylphosphoric acid (produced from 3.3 g of the dihydrate of the barium salt) and 10 g dicyclohexyl carbodiimide in 50 ml dry pyridine were stirred at r.t. for 60 hrs. Water (26 ml) was added and the solution was stirred for 30 min. The mixture was evaporated to dryness, 750 ml of methanol, 130 ml of water and 5.3 ml of acetic acid were added and the mixture was stirred overnight. The precipitate was filtered and the methanol was evaporated under reduced pressure to give 8 g of a gummy oil, which was chromatographed on 3.5×80 cm silica gel, dry column, by $CHCl_3$—$CH_3OH$—$H_2O$ 50:35:5. The column was cut to eight equal sections and the product was extracted from the third section from the top with methanol. The turbid methanol solution was concentrated to a small volume, the turbidity was removed by centrifugation and the solution was concentrated to give 2.1 g of a yellowish oil. The oil was dissolved in 5 ml of methanol and 100 ml of acetone were added. There were obtained 1.5 g of a white powder. UV and NMR indicated 50% purity. tlc, silica, $R_f$ 0.45, $CHCl_3$—$CH_3OH$—$H_2O$ (50:35:5).

d. 4-Methylumbelliferyl-$\beta$-D-(−)-galactopyranoside-6-phosphate

The crude cyanoethyl compound (1.5 g) was dissolved in a solution of 42 ml 58% $NH_4OH$ and 18 ml water and heated for 2.5 hr at 55°. The solution was centrifuged and the supernatant was evaporated to give a yellowish oil which crystallized upon adding 12 ml methanol. The white crystals were washed twice with acetone to give 0.85 g. This material was chromatographed on prep. tlc with $CHCl_3$—$CH_3OH$—$H_2O$ (60:35:5) and extracted from the silica with methanol. The solution was concentrated to a small volume, acetone was added and 0.51 g of white crystals were separated. tlc, silica, $R_f$ 0.64 in iPrOH—58% $NH_4OH$—$H_2O$ (60:5:35). The compound was 77% pure according to u.v. and enzymatic hydrolysis by alkaline phosphatase and $\beta$-D-galactosidase.

EXAMPLE 9

Conjugation of HIgG and $\beta$-galactosidase

A reaction mixture was prepared by combining 4 ml HIgG (8.34 mg/ml, 50 mM phosphate buffer, pH 7.0), 2.17 ml phosphate buffer, pH 7.0, and 20 $\mu$l of a DMF solution of m-(N-maleimidyl) benzoic acid N-hydroxy succinimide ester (10 mg/ml) added with rapid stirring. After 30 min under $N_2$ at room temperature to the reaction was added 1 ml 1 M NaOAc to adjust the pH to 5. The mixture was then chromatographed on Sephadex G25-F (2.4×20 cm), eluted with 20 mM NaOAc, pH 5.0, containing 0.15 M NaCl at a rate of 30 ml/hr, collecting 6.6 ml fractions. Fractions 5–7 were pooled. Cysteine analysis showed about 7 maleimide groups per HIgG.

The maleimide modified HIgG was diluted with phosphate buffer followed by addition to 2 ml of a $\beta$-galactosidase solution in 50 mM phosphate buffer, pH 7.0 (0.67 g/ml), to provide a final reaction volume of 14.1 ml. The following table indicates the various amounts of solutions added for the three preparations.

| Conjugate | Maleimide HIgG ml | Maleimide HIgG mg | Phosphate Buffer, pH7 0.5M ml | Phosphate Buffer, pH7 0.05M ml |
|---|---|---|---|---|
| 1 | 1.5 | 2.54 | .15 | 10.45 |
| 2 | 5.0 | 8.45 | .50 | 7.60 |
| 3 | 11.85 | 20.03 | 1.25 | — |

The reaction was carried out at R.T. for 21 hrs under $N_2$. Any remaining maleimide groups were reacted with cysteine-HCl. The solutions were concentrated under $N_2$ with an Amicon Ultrafiltration over a PM30 membrane (conjugates 1&2), PM10 membrane (conjugate 3) to a final volume including wash of about 2 ml. The three samples were then chromatographed on Biogel A5M (82×1.5 cm) with PBS, 0.05% $NaN_3$, 1 mM $Mg(OAc)_2$, eluting at 4–8 ml/hr and collecting fractions of about 2.5 ml. With Conjugate 3 as exemplary, fractions 25 to 34 were pooled and assayed. Approximately 67% of the enzyme activity was recovered as conjugate product. Based on radioactive counting of radioactively labeled HIgG, approximately 81% of the HIgG was recovered in total. The concentration of enzyme was 31.45 $\mu$g/ml, while the concentration of HIgG was 83.4 $\mu$g/ml.

EXAMPLE 10

Preparation of rabbit anti(HIgG) (Ranti(HIgG)) conjugated to Sepharose 4B beads

Into a reaction vessel was introduced 2 ml containing 7.5 mg of rabbit anti(HIgG) in 0.1 M $NaHCO_3$, pH 8.1, 0.5 M NaCl and 0.9 g CNBr activated Sepharose 4B beads and the mixture stirred at 4° for 6 hrs, followed by stirring at R.T. for 2 hrs. To the mixture was then added 0.1 volume 1 M 2-aminopropanol, pH 8.0 and the mixture stirred overnight at 4°. By employing radioactive Ranti(HIgG), it was found that 6.6 mg had coupled.

The beads (protein ~5 mg/ml packed beads) were washed by suspension in 1×PBS (0.5 hr), and then centrifuged (3×). After suspending in about ⅓ vol/vol of PBS, ~0.5 ml of the suspended beads (~0.2 ml beads) was diluted with ~1.5 ml PBS, and the solution introduced into the small probe of a model W185 Systems, Ultrasonics Inc, power 60 watts, setting ~1.5, the sample cooled in an ice-bath and sonicated for 3 min., followed by centrifugation and then an additional 2 min sonication.

EXAMPLE 11

Preparation of conjugate of o-nitrophenyl-β-galactoside and dextran a. To 7 ml of 1.8 N Na chloroacetate solution and 3 ml water was added 2 g dextran T2000 (Pharmacia), followed by the addition of 10 ml 2.5 M aq. NaOH, and the mixture heated at 70°-75° for 1.5 hr and allowed to stand overnight. To the mixture was added 2 ml glac. HOAc and the mixture then dialyzed against 10 l 5% aq. HOAc (4×24 hr) and then against deionized H$_2$O, 10 l, (4×24 hrs). By employing radioactively labeled chloroacetate, it was found that there were about 1.21 μmoles of carboxymethyl per mg of dextran.

b. To 80 ml of an aqueous solution containing 1.96 μmole of the carboxymethyldextran prepared above was added 8 ml (40 mmole) of N,N'-bis-(3-aminopropyl)piperazine and 18 g (90 mmole) EDCI and the solution allowed to stand at R.T. for 24 hrs. The reaction mixture was then dialyzed against 12 l. deionized water containing 150 g K$_2$HPO$_4$ and 75 g KH$_2$PO$_4$ (4×24 hrs) and the number of amino groups determined employing trinitrobenzenesulfonic acid was found to be 68% of the available carboxy groups.

c. To 10 ml DMF was added 387 mg 2-nitro-5-carboxyphenyl-β-galactoside, 249 mg EDCI and 151 mg N-hydroxy sucnimide and the mixture stirred at R.T. for 1 hr. To 10 ml of aqueous solution containing the aminosubstituted dextran prepared above (9.2 mM in amino groups) was added 2.5 ml of the NHS ester prepared above and the reaction mixture stored at R.T. for 24 hrs. The reaction mixture was dialyzed against water (4×) and the product assayed for o-nitrophenyl-β-galactoside groups (ONPG). The product was found to be 7.0 mM/ml in ONPG groups by UV.

In order to demonstrate the subject invention, an assay for HIgG was performed. The following table indicates the reagents employed.

| Assay Components |
|---|
| (1) Sepharose4B-(G-6-PDH)-HIgG conjugate (Ex. 1) |
| ~20mg beads/ml |
| 16.3U/ml G-6-PDH |
| 8.0μg/ml HIgG |
| (2) Rabbit anti(HIgG)-hexokinase conjugate (Ex. 2) |
| 141.5μg/ml conjugate |
| 65μg/ml rabbit anti(HIgG) |
| 76.5μg/ml HK |
| HK/rabbit anti(HIgG) 1.7 mole ratio |
| (3) Incubation buffer |
| 50mM Tris. HCl, 200mM NaCl, NAD⊕, |
| 3mM ATP, 100mM glucose, 6mM MgCl$_2$, |
| 20% w/v* sucrose. 0.05% NaN$_3$, pH8.0 |

*g/ml

To perform the assay, 8 μl of beads is added to 50 μl of incubation buffer containing varying amounts of human IgG. To the incubation mixture is added 8 μl of the rabbit anti(HIgG)-HK conjugate and the samples incubated for 30 min at 37°. To the mixture is then added 1 ml of assay buffer, the sample vortexed for approximately 3 sec and immediately aspirated into a Stasar III Spectrophotometer. The rate of NADH production is monitored for 2 min at 37° at 340 nm. The following table indicates the results.

TABLE IX

| Sample | ng HIg | mA$_{340}$/2 min | Ave | SD | CV % |
|---|---|---|---|---|---|
| 1 | 1248 | 123, 128 | 125.5 | 3.5 | 2.8 |
| 2 | 416 | 129, 133 | 131 | 2.8 | 2.1 |
| 3 | 139 | 129, 131, 128 | 129.3 | 1.5 | 1.1 |
| 4 | 46.2 | 147, 149 | 148 | 1.4 | 1.0 |
| 5 | 15.4 | 151, 165, 157 | 157.7 | 7.0 | 4.5 |
| 6 | 5.14 | 177, 155 | 166 | 15.5 | 9.3 |
| 7 | 1.71 | 170, 166 | 168 | 2.8 | 1.7 |

The preceding data can be constructed into a standard for the determination of antigen (Human IgG) in an unknown samples.

The following assay demonstrates the use of the coupled enzymes, alkaline phosphatase and β-galactosidase to provide a fluorescent compound from a non-fluorescing compound.

| Assay components: |
|---|
| Incubation Buffer - 0.1M Tris-HCl pH 8.0, 50mM NaCl, |
| 1mM MgCl$_2$ ,0.05% NaN$_3$, 1mg/ml egg |
| albumin |
| Substrate solution - 0.75mg/ml 4-MUG-6-P in 0.1M Tris-HCl |
| pH8.0, 50mM NaCl, 1mM MgCl$_2$ |
| Quenching solution - 0.4M Glycine - NaOH, pH10.3 |
| Sepharose 4B-β-D-Galactosidase-HIgG-as prepared, dil. 1:4 |
| with incubation buffer |
| without egg albumin |
| RIgG-AP-II - diluted 1:4 with incubation |
| buffer |
| HIgG and non-immunogenic RIgG - solutions in incubation |
| buffer |
| Assay Protocol |
| 1. Preincubation: RIgG-AP-II (20μl) is added to 100μl of |
| incubation buffer containing HIgG in |
| the amounts indicated below: |

| Sample | ng of HIgG |
|---|---|
| 1 | 0 |
| 2 | 24 |
| 3 | 48 |
| 4 | 150 |
| 5 | 300 |
| 6 | 600 |
| 7 | 1200 |

Samples are stirred for 1hr at r.t.

2. Incubation: 20μl of beads suspension is added and the samples are stirred for 2hrs at r.t.
3. Reaction: 0.35ml of substrate solution is added, vortexed and allowed to stay at r.t. without stirring for 5 min.
4. Quenching: 0.5ml of quenching solution is added, vortexed and fluorescence ($\lambda_{ex}$ — $\lambda_{em}$ — 447) is measured.

The following fluorescence values were recordered for samples 1 through 7:

| Sample | ngHIgG | 10$^{-10}$M HIgG | F |
|---|---|---|---|
| 1 | 0 | 0 | 457,404 |
| 2 | 24 | 1.5 | 411 |
| 3 | 48 | 3 | 372 |
| 4 | 150 | 9.4 | 303,300 |
| 5 | 300 | 18.8 | 231 |
| 6 | 600 | 37.5 | 211 |
| 7 | 1200 | 75 | 228,203 |

These data can be constructed into a standard curve for the defermination of antigen (HIgG) in an unknown sample.

An assay for HIgG was performed as follows employing sonicated Sepharose 4B beads conjugated with RantiHIgG, The materials employed were the Sepharose 4B-RantiHIgG suspended at 0.1 ml/ml in buffer (PBS, 5 mM N$_3$), the ONPG-Dextran (2 M mol. wt.) 10 mM NaN$_3$, 0.1% RSA, the HIgG-$\beta$-galactosidase conjugate (1) (4 mM) in PBS, 0.1% RSA, 5 mM N$_3$, 0.1 mM Mg(OAc)$_2$ (9 $\mu$g/ml $\beta$-galactosidase) and RIgG or HIgG (50 mg/ml) in PBS, 10 mM NaN$_3$.

The protocol employed was as follows: 50 $\mu$l beads or 50 $\mu$l buffer is combined with 50 $\mu$l RIgG or HIgG or buffer and incubated 30 min at RT followed by the addition of 50 $\mu$l of the enzyme conjugate. After incubating for 30 min at RT 0.1 ml of the ONPG-dextran substrate and 0.8 ml of the buffer, 0.1%, RSA, 0.1 mM Mg is added to a final volume of 1.05 ml which is promptly aspirated into a spectrophotometer cell. The reaction mixture is then read at 37° at 420 nm by taking readings at 10 and 40 sec after addition of the substrate. The results are reported as the $\Delta$ODmin$^{-1}$.

| Tube | Beads[1] | RIgG | HIgG | Buffer | Rate min$^{-1}$ | % Activity[2] |
|---|---|---|---|---|---|---|
| 1 | − | − | + | − | 0.920 | 103 |
| 2 | − | − | − | + | 0.894 | 100 |
| 3 | + | − | − | + | 0.428 | 48 |
| 4 | + | − | + | − | 0.906 | 101 |

[1] + presence; − absence
[2] % of activity of enzyme conjugate by itself in buffer with substrates.

The above results show that the beads inhibit the reaction of the galactosidase conjugate with the macromolecular substrate when the conjugate is bound to the beads, but has no effect on the galactosidase when the conjugate is not bound to the beads. When HIgG is added to block the binding of the HIgG-$\beta$-galactosidase conjugate to the bead, the galactosidase retains its activity.

A similar assay as described above was performed employing the following reagents:
Buffer: PBS, 0.1% RSA, 5 mM NaN$_3$, 0.1 mM Mg(OAc)$_2$
Particles: RantiHIgG in buffer at 0.02 ml/ml
Conjugate: Ex. 9 in buffer at 9 $\mu$g $\beta$-galactosidase/ml
HIgG: 5.0 mg/ml in PBS, 5 mM NaN$_3$, further diluted as indicated.
Substrate: ONPG-Dextran (2 M mol. wt.), 4 mM ONPG in PBS, 5 mM NaN$_3$ The protocol was as follows: combine each of 50 $\mu$l of the conjugate solution, 50 $\mu$l of HIgG solution and 50 $\mu$l of the particles with 100 $\mu$l of buffer and combine the diluted reagents in that order. Incubate at R.T. for 3 hrs. Add 0.1 ml substrate and 0.4 ml buffer and aspirate the mixture into a spectrophotometer cell and read at 37° at 10 and 40 sec after adding the substrate. The following table indicates the results.

| Tube | Particles[1] | HIgG dilution | Rate (min$^{-1}$) | Activity % |
|---|---|---|---|---|
| 1 | − | inf. | 0.776 | (100) |
| 2 | + | inf. | 0.186 | 24 |
| 3 | + | 16384 | 0.150 | 19 |
| 4 | + | 4096 | 0.196 | 25 |
| 5 | + | 1024 | 0.328 | 42 |
| 6 | + | 256 | 0.548 | 71 |
| 7 | + | 64 | 0.702 | 90 |
| 8 | + | 16 | 0.762 | 98 |
| 9 | + | 4 | 0.768 | 99 |
| 10 | + | 1 | 0.762 | 98 |

[1] − buffer; + particles
[2] inf-HIgG solution substituted with buffer. HIgG solution serially diluted four-fold The above results demonstrate an assay for HIgG covering a concentration range of about 10$^3$ fold ranging from about 3 to 0.03 $\mu$M.

The subject method provides for a novel accurate technique for measuring extremely low concentrations of a wide variety of ligands, both haptenic and antigenic, and receptors. The method is rapid, requiring only a short measurement time, and can be applied to a wide variety of instrumentation which is presently commercially available. In addition, the method avoids any requirement for pure antigen or pure antibody for use in the preparation of the various reagents. So long as there is a significant number of the members of the specific binding pair bound to the particle, the presence of other extraneous material bound to the particle will not interfere with the assay. Similarly, as to the homologous member, which is labeled, the substantial enhancement of signal observed as a result of combining the members of the signal producing system in the particle will diminish the effect of the background from the bulk solution.

The subject method is extremely versatile in allowing for a wide variety of different combinations for producing signals. Furthermore, by varying the nature of the particle, the sensitivity of the system can be further enhanced. In addition, the subject system allows for substantial reduction in background, by providing for macromolecular materials which can interact with materials in the bulk solution, so as to diminish their ability to affect the detectible signal. For example, where enzymes are used in combinations, an inhibitor for the enzyme in the bulk solution can be employed which is of sufficient size so as to be substantially inhibited from inhibiting the enzyme in the particle.

Although the foregoing invention has been described in some detail by way of illustration and example for purposes of clarity of understanding, it will be obvious that certain changes and modifications may be practiced within the scope of the appended claims.

What is claimed is:

1. An assay method for determining the presence in a sample of an analyte which is a member of a specific binding pair consisting of ligand and its homologous receptor;

said method employing:
(a) a continuous aqueous medium;
(b) discrete dispersable solid particles to which is conjugated one of the members of said pair to provide a particle conjugate, said particle conjugate defining an environment about said conjugated member of said pair different from said aqueous medium, wherein when a signal label is bound to said particle conjugate, the signal resulting from such signal label is different from the signal resulting from the signal label in said continuous aqueous medium;
(c) a signal producing system capable of producing a measurable signal, the level of said signal being affected by the extent to which said signal producing system is within the environment of said particles;

(d) at least one member of said signal producing system being conjugated to a pair member to provide a signal label conjugate, wherein the amount of signal label conjugate bound to said particle conjugate is related to the amount of analyte in said aqueous medium;

said method comprising:

combining in an aqueous assay medium,
(a) said sample;
(b) said particle conjugate substantially uniformly dispersed in said medium;
(c) said signal label conjugate;
(d) the homologous member of said specific binding pair, where the analyte, particle conjugate, and signal label conjugate are the same member of the specific binding pair; and
(e) any remaining members of said signal producing system;

with the proviso that when the analyte is a first receptor, said member of said pair conjugated to said particle can be the homologous ligand or receptor for said first receptor, and said member of said signal label conjugate can be receptor for said first receptor or the homologous ligand respectively; and determining the level of said signal in said aqueous assay medium as compared to an assay medium having a known amount of analyte.

2. A method according to claim 1, wherein said aqueous assay medium is at a temperature in the range of about 10° to 50° C. and at a pH in the range of about 5 to 10.

3. A method according to claim 2, wherein said signal producing system has at least a first enzyme.

4. A method according to claim 3, wherein said measurable signal is based on a compound being detected by light absorption at a wavelength greater than 300 nm.

5. A method according to claim 3, wherein said measurable signal is based on fluorescent light emission at a wavelength greater than 350 nm.

6. A method according to claim 3, wherein said signal producing system includes ligand-enzyme conjugate.

7. A method according to claim 3, wherein said signal producing system includes receptor-enzyme conjugate.

8. A method according to claim 7, wherein said signal producing system includes a macromolecular enzyme inhibitor.

9. A method according to claim 3, wherein said signal producing system includes a macromolecular substrate reagent for said first enzyme.

10. A method according to any one of claims 3 to 8, wherein said first enzyme is an oxidoreductase.

11. A method according to any of claims 3 to 9, wherein said first enzyme is a hydrolase.

12. A method according to claim 3, wherein said signal producing system includes a second enzyme, which is related to said first enzyme, by the product of one of the enzymes being the substrate of the other of said enzymes.

13. A method according to claim 12, wherein said first enzyme and ligand is conjugated to said particle and said second enzyme is conjugated to receptor.

14. A method according to claim 12, wherein said first enzyme and receptor is conjugated to said particle and said second enzyme is conjugated to ligand.

15. A method according to claim 2, wherein said signal producing system includes a fluorescer emitting light at a wavelength greater than 350 nm.

16. A method according to claim 15, wherein said fluorescer is conjugated to a specific binding pair member.

17. A method according to claim 16, wherein said signal producing system includes antifluorescer.

18. A method according to claim 16, wherein said particle conjugate is ligand bound to said particle.

19. A kit for use in an immunoassay method according to claim 1 comprising in combination in relative amounts to substantially optimize the sensitivity of said immunoassay a particle conjugate having both a member of said specific binding pair conjugated to discrete porous solid particles and a first enzyme, and a second enzyme conjugated to a member of said specific binding pair to provide a signal label conjugate, wherein said enzymes are related by the product of one being the substrate of the other.

20. A kit according to claim 19, wherein said particle conjugate has ligand bound to said particle and said signal label conjugate has enzyme bound to receptor.

21. A kit for use in an immunoassay method according to claim 1 comprising in combination in relative amounts to substantially optimize the sensitivity of said immunoassay a particle conjugate having a ligand conjugated to discrete porous solid particles, a enzyme conjugated to antiligand, and a substrate for said enzyme covalently bonded to a hub nucleus.

22. A kit according to claim 21, wherein said ligand is a $\gamma$-globulin, sand enzyme is $\beta$-galactosidase, and including o-nitrophenyl galactoside as said enzyme substrate.

23. An assay method for determining the presence in a sample of a ligand analyte, wherein the ligand with its homologous antiligand defines a specific binding pair, wherein said method employs (1) a medium comprised of an aqueous buffered continuous phase at a pH in the range of about 6.5 to 9.5 and a discontinuous solid phase of discrete porous dispersable particles to which is conjugated one of the members of said specific binding pair to provide a particle conjugate; and (2) a signal producing system capable of producing a measureable signal and having at least one member of said system conjugated to a member of said specific binding pair to provide a signal label conjugate, said particle conjugate defining an environment which affects the level of said measurable signal different from said aqueous medium, so that said measurable signal varies in relation to the partitioning of said signal producing system between said particles and said aqueous medium, said partitioning being related to the amount of analyte in said medium;

said method comprising:

combining in said aqueous medium,
(a) said sample;
(b) said particle conjugate substantially uniformly dispersed;
(c) said signal label conjugate;
(d) the homologous member of said specific binding pair, when said analyte, particle conjugate and signal label conjugate have the same member of said specific binding pair; and
(e) any additional members of said signal producing system, whereby said signal label conjugate is partitioned between said aqueous medium and said particle conjugate to a degree dependent upon the amount of ligand in said sample; and determining the level of said signal in said aqueous medium as compared to an assay medium having a known amount of ligand.

24. A method according to claim 23, wherein said particle conjugate has ligand as said specific binding pair member, said signal label conjugate has antiligand as said specific binding pair member, and said signal producing system has an enzyme as a member.

25. A method according to claim 24, wherein said signal producing system includes a macromolecular enzyme inhibitor.

26. A method according to claim 24, wherein said signal producing system has a macromolecular enzyme substrate reagent as a member.

27. A method according to claim 24, wherein said signal producing system has a second enzyme as a member.

28. A method according to claim 23, wherein said particle conjugate has ligand as said specific binding pair member, said signal label conjugate has antiligand as said specific binding pair member, and said signal producing system has a fluorescer emitting light at a wavelength greater than 350 nm as a member.

29. A method according to claim 28, wherein said signal producing system includes fluorescer bound to antiligand.

30. An assay method for determining the presence in a sample of a ligand analyte, wherein the ligand with its homologous antiligand define a specific binding pair, wherein said method employs (1) a medium comprised of an aqueous buffered continuous phase at a pH in the range of about 6.5 to 9.5 and a discontinuous solid phase of dispersable porous discrete particles to which is conjugated one of the members of said specific binding pair and a first enzyme to provide a particle conjugate and (2) a signal producing system capable of producing a measurable signal and having a second enzyme conjugated to a member of said specific binding pair to provide a signal label conjugate, wherein said first and second enzymes with appropriate substrates and cofactors define said signal producing system and said first and second enzymes are related by the product of one being the substrate of the other, said particle conjugate defining an environment which affects the production of said signal differently from said aqueous medium, so that said measurable signal varies in relation to the partitioning of said signal label conjugate between said particles and said aqueous medium, said partitioning being related to the amount of analyte in said medium, said method comprising:
combining in said aqueous medium,
(a) said sample;
(b) said particle conjugate substantially uniformly dispersed in said aqueous medium;
(c) said signal label conjugate;
(d) the homologous member of said specific binding pair, when said analyte, particle conjugate and signal label conjugate in said aqueous medium have the same member; and
(e) any additional members of said signal producing system, whereby said signal label conjugate will be partitioned between said aqueous medium and said particle conjugate to a degree dependent upon the amount of ligand in said sample; and determining the level of said signal in said aqueous medium as compared to an assay medium having a known amount of ligand.

31. A method according to claim 30, wherein said particle is a cross-linked polysaccharide.

32. A method according to claim 30, wherein said particle is a glass.

33. A method according to claim 30, where said first enzyme is a hydrolase.

34. A method according to claim 33, wherein said second enzyme is a hydrolase.

35. A method according to claim 34, wherein said first enzyme is alkaline phosphatase, said second enzyme is a glycosidase and said substrate is a phosphorylated glycosidyl ether of a fluorescent hydroxylic compound, which fluoresces only as the free hydroxyl under the conditions of the assay.

36. A method according to claim 35, wherein said glycosidase is beta-galactosidase and said fluorescent compound is umbelliferone.

37. A method according to claim 30, wherein said first enzyme is a transferase.

38. A method according to claim 37, wherein said second enzyme is an oxidoreductase.

39. A method according to claim 38, wherein said transferase is a hexokinase and said oxidoreductase is an NAD dependent dehydrogenase.

40. A method according to claim 39, wherein said NAD dependent dehydrogenase is glucose-6-phosphate dehydrogenase and the substrate for said hexokinase is glucose.

41. An assay method for determining the presence in a sample of a ligand analyte, wherein the ligand with its homologous antiligand defines a specific binding pair, wherein said method employs (1) a medium comprised of an aqueous buffered continuous phase at a pH in the range of about 6.5 to 9.5 and a discontinuous solid phase of discrete porous dispersable particles to which ligand is conjugated to provide a particle conjugate; and (2) a signal producing system capable of producing a measurable signal having a first enzyme conjugated to antiligand to provide a signal label conjugate, said particle conjugate defining an environment which affects the level of said measurable signal different from said aqueous medium, so that said measurable signal varies in relation to the partitioning of said signal producing system between said particles and said aqueous medium, said partitioning being related to the amount of analyte in said medium;

said method comprising:
combining in said aqueous medium,
(a) said sample;
(b) said particle conjugate substantially uniformly dispersed;
(c) said signal label conjugate;
(d) any additional members of said signal producing system, whereby said signal label conjugate is partitioned between said aqueous medium and said particle conjugate to a degree dependent upon the amount of ligand in said sample; and determining the level of said signal in said aqueous assay medium as compared to an assay medium having a known amount of ligand.

42. A method according to claim 41, wherein said signal producing system includes a molecular enzyme substrate.

43. A method according to claim 42, wherein said enzyme is β-galactosidase and said macromolecular substrate is o-nitrophenyl-β-galactoside bonded to dextran of at least 40,000 molecular weight.

44. An assay method for determining the presence in a sample of an antiligand analyte, wherein the antiligand with its homologous ligand defines a specific binding pair wherein said method employs (1) a medium comprised of an aqueous buffered continuous phase at a pH in the range of about 6.5 to 9.5 and a discontinuous solid phase of discrete porous dispersable particles to which is conjugated one of the members of said specific binding pair to provide a particle conjugate; and (2) a signal producing system capable of producing a measurable signal and having at least one member of said system conjugated to a member of said specific binding pair to provide a signal label conjugate, said particle conjugate defining an environment which affects the level of said measurable signal different from said aqueous medium, so that said measurable signal varies in relation to the partitioning of said signal producing system between said particles and said aqueous medium, said partitioning being related to the amount of analyte in said medium;

said method comprising:

combining in said aqueous medium, (a) said sample;

(b) said particle conjugate substantially uniformly dispersed;

(c) said signal label conjugate;

(d) the homologous member of said specific binding pair, when said analyte, particle conjugate and signal label conjugate have the same member of said specific binding pair; and (e) any additional members of said signal producing system, whereby said signal label conjugate is partitioned between said aqueous medium and said particle conjugate to a degree dependent upon the amount of antiligand in said sample; and determining the level of said signals in said assay medium as compared to an assay medium having a known amount of antiligand.

45. A method according to claim 44, wherein antiligand and its homologous receptor (anti(antiligand)) defines a second specific binding pair and said signal label conjugate has one member of said signal producing system conjugated to anti(antiligand).

46. A composition comprising a discrete porous particle of a size in the range of about 500 nm to 100μ to which is conjugated a first enzyme and at least one molecule of a member of a specific binding pair consisting of ligand and antiligand; and a second enzyme which is a member of a signal producing system covalently bonded to a member of said specific binding pair, wherein said signal producing system member is bound to said particle through the intermediacy of the non-covalent binding of members of said specific binding pair and said first and second enzymes are characterized by the product of one of said enzymes being the substrate of the other of said enzymes.

* * * * *